United States Patent [19]

Johansen et al.

[11] Patent Number: 5,767,085
[45] Date of Patent: Jun. 16, 1998

US005767085A

[54] COMPOUNDS WITH GROWTH HORMONE RELEASING PROPERTIES

[75] Inventors: Nils Langeland Johansen, Copenhagen Ø; Jesper Lau, Farum; Kjeld Madsen, Værløse; Behrend Friedrich Lundt, Kokkedal; Henning Thøgersen, Farum; Birgit Sehested Hansen, Stenløse; Bernd Peschke, Måløv, all of Denmark

[73] Assignee: Novo Nordisk A/S, Bagsvaerd, Denmark

[21] Appl. No.: 448,623

[22] PCT Filed: Dec. 22, 1994

[86] PCT No.: PCT/DK94/00485

§ 371 Date: Jun. 6, 1995

§ 102(e) Date: Jun. 6, 1995

[87] PCT Pub. No.: WO95/17423

PCT Pub. Date: Jun. 29, 1995

[30] Foreign Application Priority Data

Dec. 23, 1993 [DK] Denmark .................... 1439/93
Jan. 28, 1994 [DK] Denmark .................... 0121/94
Oct. 14, 1994 [DK] Denmark .................... 1191/94

[51] Int. Cl.$^6$ .......... A61K 38/05; A61K 38/06; A61K 38/07; A61K 38/08

[52] U.S. Cl. ................ 514/17; 514/18; 514/19; 530/329; 530/330; 530/331; 546/265; 546/280.4; 546/281.1; 546/337; 548/454; 548/455; 548/465; 548/496; 549/58; 549/59; 549/77; 562/445; 562/448; 562/450; 564/155; 564/164

[58] Field of Search ..................... 514/17, 18, 19; 530/330, 329, 331; 564/155, 164; 562/445, 448, 450; 549/58, 59, 77; 548/454, 455, 465, 496; 546/265, 277.4, 280.4, 281.1, 337

[56] References Cited

U.S. PATENT DOCUMENTS

| | | | |
|---|---|---|---|
| 4,223,019 | 9/1980 | Momany | 424/177 |
| 4,223,020 | 9/1980 | Momany | 530/330 |
| 4,228,156 | 10/1980 | Momany | 530/331 |
| 4,410,512 | 10/1983 | Bowers | 930/20 |

FOREIGN PATENT DOCUMENTS

WO 95/14666  6/1995  WIPO.

*Primary Examiner*—Jeffrey E. Russel
*Attorney, Agent, or Firm*—Steve T. Zelson; Elias J. Lambiris

[57] ABSTRACT

Compounds of the formula A—B—C—D(—E)$_p$ are used to stimulate the release of growth hormone from the pituitary.

18 Claims, No Drawings

COMPOUNDS WITH GROWTH HORMONE RELEASING PROPERTIES

FIELD OF INVENTION

The present invention relates to novel peptide derivatives, compositions containing them, and their use for treating medical disorders resulting from a deficiency in growth hormone.

BACKGROUND OF THE INVENTION

Growth hormone is a hormone which stimulates growth of all tissues capable of growing. In addition, growth hormone is known to have a number of effects on metabolic processes, e.g., stimulation of protein synthesis and free fatty acid mobilization and to cause a switch in energy metabolism from carbohydrate to fatty acid metabolism. Deficiency in growth hormone can result in a number of severe medical disorders, e.g., dwarfism.

Growth hormone is released from the pituitary. The release is under tight control of a number of hormones and neurotransmitters either directly or indirectly. Growth hormone release can be stimulated by growth hormone releasing hormone (GHRH) and inhibited by somatostatin. In both cases the hormones are released from the hypothalamus but their action is mediated primarily via specific receptors located in the pituitary. Other compounds which stimulate the release of growth hormone from the pituitary have also been described. For example arginine, L-3,4-dihydroxyphenylalanine (L-Dopa), glucagon, vasopressin, PACAP (pituitary adenylyl cyclase activating peptide), muscarinic receptor agonists and a synthethic hexapeptide, GHRP (growth hormone releasing peptide) release endogenous growth hormone either by a direct effect on the pituitary or by affecting the release of GHRH and/or somatostatin from the hypothalamus.

In disorders or conditions where increased levels of growth hormone is desired, the protein nature of growth hormone makes anything but parenteral administration non-viable. Furthermore, other directly acting natural secretagogues, e.g., GHRH and PACAP, are longer polypeptides for which reason oral administration of them is not viable.

The use of shorter peptides for increasing the levels of growth hormone in mammals has previously been proposed, e.g. in EP 18 072, EP 83 864, WO 89/07110, WO 89/01711, WO 89/10933, WO 88/9780, WO 83/02272, WO 91/18016, WO 92/01711 and WO 93/04081.

The composition of growth hormone releasing peptides or peptide derivatives is important for their growth hormone releasing potency as well as their bioavailability. It is therefore the object of the present invention to provide peptides with growth hormone releasing properties which have improved properties relative to known peptides of this type.

SUMMARY OF THE INVENTION

Accordingly, the present invention relates to a compound of general formula I

A—B—C—D(—E)$_p$    I wherein p is 0 or 1;
A is hydrogen or $R^1$—(CH$_2$)$_q$—(X)$_r$—(CH$_2$)$_s$—CO—, wherein
q is 0 or an integer between 1 and 5;

r is 0 or 1;
s is 0 or an integer between 1 and 5;
$R^1$ is hydrogen, imidazolyl, guanidino, piperazino, morpholino, piperidino or N($R^2$)—$R^3$, wherein each of $R^2$ and $R^3$ is independently hydrogen or lower alkyl optionally substituted by one or more hydroxyl, pyridinyl or furanyl groups; and
X, when r is 1, is —NH—, —CH$_2$—, —CH=CH—,

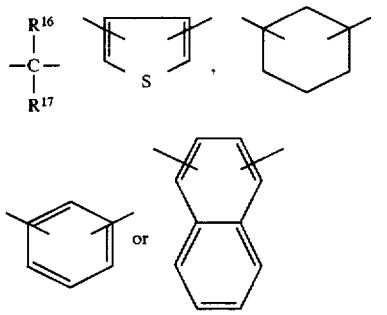

wherein each of $R^{16}$ and $R^{17}$ is independently hydrogen or lower alkyl;

B is (G)$_t$—(H)$_u$ wherein
t is 0 or 1;
u is 0 or 1;
G and H are amino acid residues selected from the group consisting of natural L-amino acids or their corresponding D-isomers, or non-natural amino acids such as 1,4-diaminobutyric acid, aminoisobutyric acid, 1,3-diaminopropionic acid, 4-aminophenylalanine, 3-pyridylalanine, 1,2,3,4-tetrahydroisoquinoline-3-carboxylic acid, 1,2,3,4-tetrahydronorharman-3-carboxylic acid, N-methylanthranilic acid, anthranilic acid, N-benzylglycine, 3-aminomethylbenzoic acid, 3-amino-3-methyl butanoic acid, sarcosine, nipecotic acid or iso-nipecotic acid; and wherein, when both t and u are 1, the amide bond between G and H is optionally substituted by

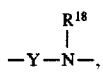

wherein Y is >C=O or

and $R^{18}$ is hydrogen, lower alkyl or lower aralkyl;

C is a D-amino acid of formula —NH—CH((CH$_2$)$_w$—$R^4$)—CO—wherein w is 0, 1 or 2; and
$R^4$ is selected from the group consisting of

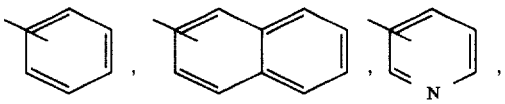

-continued

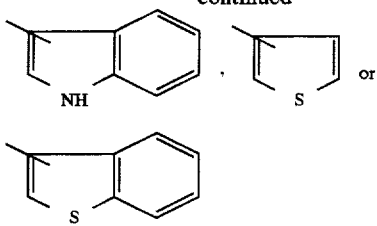

each of which is optionally substituted with halogen, lower alkyl, lower alkyloxy, lower alkylamino, amino or hydroxy;

D, when p is 1, is a D-amino acid of formula —NH—CH(($CH_2$)$_k$—$R^5$)—CO— or, when p is 0, D is —NH—CH(($CH_2$)$_l$—$R^5$)—$CH_2$—$R^6$ or —NH—CH(($CH_2$)$_m$—$R^5$)—CO—$R^6$, wherein
k is 0, 1 or 2;
l is 0, 1 or 2;
m is 0, 1 or 2;
$R^5$ is selected from the group consisting of

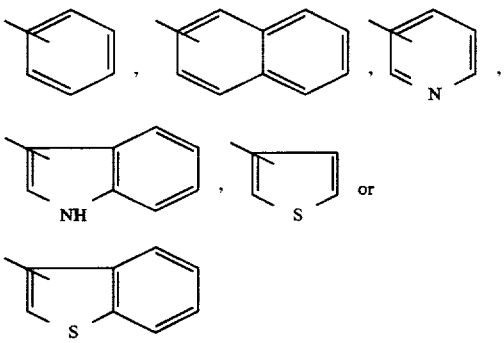

each of which is optionally substituted with halogen, alkyl, alkyloxy amino or hydroxy; and $R^6$ is piperazino, morpholino, piperidino, —OH or —N($R^7$)—$R^8$, wherein each of $R^7$ and $R^8$ is independently hydrogen or lower alkyl;

E, when p is 1, is —NH—CH($R^{10}$)—($CH_2$)$_v$—$R^9$, wherein
v is 0 or an integer between 1 and 8;
$R^9$ is hydrogen, imidazolyl, guanidino, piperazino, morpholino, piperidino, 1$^{19}$

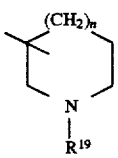

wherein n is 0, 1 or 2, and $R^{19}$ is hydrogen or lower alkyl,

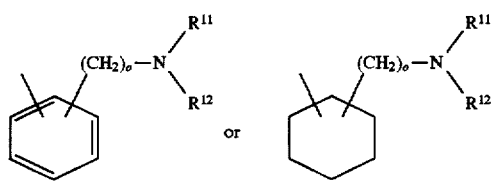

wherein o is an integer from 1 to 3, or N($R^{11}$)—$R^{12}$, wherein each of $R^{11}$ and $R^{12}$ $^2$ is independently hydrogen or lower alkyl, or

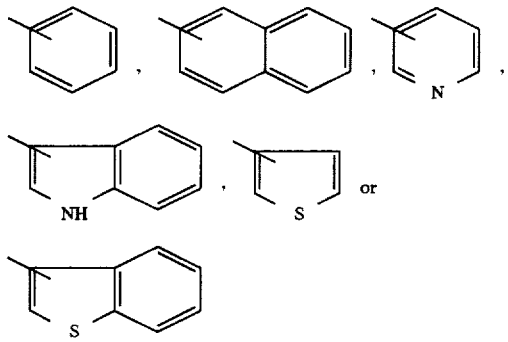

each of which is optionally substituted with halogen, alkyl, alkyloxy, amino, alkylamino, hydroxy, or the Amadori rearrangement product from an amino group and a hexapyranose or a hexapyranosyl-hexapyranose and $R^{10}$, when p is 1, is selected from the group consisting of —H, —COOH, —$CH_2$—$R^{13}$, —CO—$R^{13}$ or —$CH_2$—OH, wherein $R^{13}$ is piperazino, morpholino, piperidino, —OH or —N($R^{14}$)—$R^{15}$, wherein each of $R^{14}$ and $R^{15}$ is independently hydrogen or lower alkyl;

the amide bond between B and C or, when t and u are both 0, between A and C being optionally substituted by

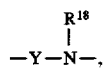

wherein Y is >C=or

and $R^{18}$ is hydrogen, lower alkyl or lower aralkyl, or, when p is 1, the amide bond between D and E being optionally substituted by

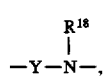

wherein Y and $R^{18}$ are as indicated above; or a pharmaceutically acceptable salt thereof.

It is believed that peptide derivatives of formula I exhibit an improved resistance to proteolytic degradation by enzymes due to the presence of adjacent D-amino acids in the peptide sequence, optionally combined with the substitution of an amide bond (—CO—NH—) by

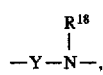

as indicated above, e.g. aminomethylene (—$CH_2$—NH—) and/or modification at the N- or C-terminal end of the peptide. The increased resistance to proteolytic degradation combined with the reduced size of the peptide derivatives of the invention is expected to improve their bioavailability compared to that of the peptides suggested in the prior literature.

In the present context, the term "lower alkyl" is intended to indicate alkyl with 1-6 carbon atoms, in particular methyl, ethyl, propyl, iso-propyl, butyl, pentyl or hexyl. The term "halogen" is intended to include Cl, F, Br and I. In the terms "lower alkyloxy", "lower aralkyl" and "lower alkylamino", the lower alkyl moiety has the meaning indicated above.

DETAILED DESCRIPTION OF THE INVENTION

In a preferred embodiment of the compound of formula I, p is 1. In another preferred embodiment of the compound of formula I, A is hydrogen or, alternatively, $R^1$—$(CH_2)_q$-$(X)_r$—$(CH_2)_s$—CO—, wherein $R^1$ is 3-imidazolyl, q is 2, r is 0 and s is 0; or wherein $R^1$ is $NH_2$, q is 1, r is 1, X is disubstituted benzene preferably substituted in the 1 and 3 positions, and s is 0; or wherein $R^1$ is NH, q is 1, r is 1, X is disubstituted thiophene preferably substituted in the 3 and 2 positions, and S is 0. When t is 1, G in the compound of formula I is preferably Ala, Gly, Aib, sarcosine, nipecotic acid or isonipecotic acid. When u is 1, H is preferably His, Phe, Tic, Phe(4—$NH_2$), 3-Pyal, Gly, Ala, Sar, Pro, Tyr, Arg, Orn, 3-aminomethylbenzoic acid or D-Phe. C in the compound of formula I is preferably D-2-naphthylalanine (D-2Nal), D-1-naphthylalanine (D-1Nal), D-Phe or D-Trp. D in the compound of formula I is preferably D-Phe, D-1N a l, D-2Nal, D-Trp, 3-Pyal, D-Phe(4F), D-Tyr or Phe-$NH_2$.

E in the compound of formula I is preferably Lys—$NH_2$, NH—(2-(1-piperazino)ethyl), NH—(2-(1-morpholino)propyl), NH—(2-aminoethyl), NH—(4-aminomethylbenzyl), NH—(benzyl), Lys—OH, NH—(1-hydroxy-6-amino-2S-hexyl), NH—(2-(1-methyl-2-pyrrolidinyl)ehtyl), or

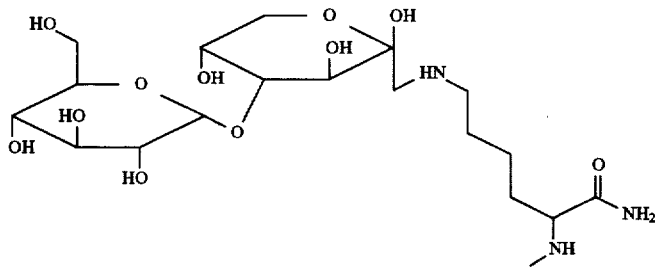

$R^4$ in the compound of formula I is preferably 2-naphthyl. $R^1$ is preferably phenyl, v is preferably 2-6, and $R^9$ is $NH_2$, morpholinoethyl, morpholinopropyl or (1-methylpyrrolidinyl)ethyl. R' is preferably —COOH, —$CH_2$—OH, —H, —$CONH_2$ or —CON$(CH_3)_2$.

Examples of specific compounds of the present invention are

H-Ala- Hisψ(CH₂NH)D-2Nal-D-Phe-Lys-NH₂
H-Ala-Ala-D-2Nal-D-Phe-Lys-NH₂
H-His-D-2Nal-D-Phe-Lys-NH₂
(3-(4-Imidazolyl)propionyl)-D-2Nal-D-Phe-Lys-NH₂
H-D-Lys-D-2Nal-D-Phe-Lys-NH₂
H-5Apent-His-D-2Nal-D-Phe-Lys-NH₂
H-D-Ala-D-2Nal-D-Phe-Lys-NH₂
H-5Apent-D-2Nal-D-Phe-Lys-NH₂
(n-Propyl)-His-D-2Nal-D-Phe-Lys-NH₂
H-Ala-3Pyal-D-2Nal-D-Phe-Lys-NH₂
H-Ala-Phe(4-NH₂)-D-2Nal-D-Phe-Lys-NH₂
H-D-Ala-His-D-2Nal-D-Phe-Lys-NH₂
(2-(4-Imidazolyl)acetyl)-D-2Nal-D-Phe-Lys-NH₂
(3-(4-Imidazolyl)acryloyl)-D-2Nal-D-Phe-Lys-NH₂
(3-Aminomethyl benzoyl)-D-2Nal-D-Phe-Lys-NH t
(3-Aminophenylacetyl)-D-2Nal-D-Phe-Lys-NH₂
(4-Aminophenylacetyl)-D-2Nal-D-Phe-Lys-NH₂
(3-Aminocrotonoyl)-D-2Nal-D-Phe-Lys-NH₂
(4-Piperidino-carboxyl)-D-2Nal-D-Phe-Lys-NH₂
H-Ala-His-D-2Nal-D-Phe-NH₂
(H-Ala-His-D-2Nal-D-Phe-NH)hexane
6-(H-Ala-His-D-2Nal-D-Phe-NH)hexylamine
5-(H-Ala-His-D-2Nal-D-Phe-NH)pentylanaine
H-Ala-His-D-2Nal-D-Pheψ(CH.NH)Lys-NH₂
H-Ala-His-D-2Nal-D-Phe-Lys-OH
(2S)-(H-Ala-His-D-2Nal-D-Phe-NH)-6-aminohexanol
(2-(H-Ala-His-D-2Nal-D-Phe-NH)ethyl)benzene
2-(H-Ala-His-D-2Nal-D-Phe-NH)ethylamine
4-((H-Ala-His-D-2Nal-D-Phe-NH)methyl)benzylamine
H-Ala-His-D-2Nal-D-Phe-Lys(maltosyl)-NH₂
H-Ala-His-D-2Nal-D-Phe-Phe-NH₂
H-Ala-His-D-2Nal-D-Phe-D-Phe-NH₂
H-Ala-His-D-Phe-D-Phe-Lys-NH₂
H-Ala-His-D-Trp-D-Phe-Lys-NH₂
H-His-D-2Nal-D-Trp-Lys-NH₂
H-Ala-His-D-lNal-D-Phe-Lys-NH₂
H-Ala-Phe-D-2Nal-D-Phe-Lys-NH₂
H-Ala-His-D-2Nal-D-Phe-Lys(maltosyl)-NH₂
(2R)-(H-Ala-His-D-2Nal-D-Phe-Lys-NH)-3phenylpropylamine H-Ala-N-Me-(2-aminobenzoyl)-D-2Nal-D-Phe-Lys-NH₂
(3-(Methylaminomethyl)benzoyl)-D-2Nal-D-Phe-Lys-NH₂
(4-(Aminomethyl)benzoyl)-D-2Nal-D-Phe-Lys-NH₂
H-His-Ala-D-2Nal-D-Phe-Lys-NH₂
4-(H-Ala-His-D-2Nal-D-Phe-NH)butylamine
3-(H-Ala-His-D-2Nal-D-Phe-NH)propylamine
(3-(Dimethylaminomethyl)benzoyl)-D-2Nal-D-Phe-Lys-NH₂
(3-Amino-3-methylbutanoyl)-D-2Nal-D-Phe-Lys-NH₂
(3-Aminomethylbenzoyl)-D-hPhe-D-Phe-Lys-NH₂
(3-Aminomethylbenzoyl)ψ(CH₂NH)D-2Nal-D-Phe-Lys-NH₂
(3-Aminomethylbenzoyl)-D-2Nal-D-hPhe-Lys-NH₂
(3-Amino-3-methylbutanoyl)-His-D-2Nal-D-Phe-Lys-NH₂
(3-Aminomethylbenzoyl)-D-2Nal-N-Bzl-Gly-Lys-NH₂
(2S)-(3-aminomethylbenzoyl) *(CH₂NH)-D-2Nal-D-Phe-NH)-6-aminohexanol (2S)-((3-aminomethylbenzoyl)-D-2Nal-D-Phe-NH)-6-aminohexanol
(3-Aminomethylbenzoyl)-D-2Nal-D-Thial-Lys-NH$_2$
(2S)-(H-Aib-His *(CH$_2$NH)-D-2Nal-D-Phe-NH)-6-aminohexanol
($^3$-Aminomethylbenzoyl)-D-2Nal-D-3Pyal-Lys-NH$_2$
(3-Aminomethylbenzoyl)-D-2Nal-D-Phe(4-F)-Lys-NH$_2$
(3-Aminomethylbenzoyl)-D-2Nal-D-Phe(4-OMe)-Lys-NH$_2$
(2-Aminomethylphenylacetyl)-D-2Nal-D-Phe-Lys-NH$_2$
(2-Aminomethylbenzoyl)-D-2Nal-D-Phe-Lys-NH$_2$
2-(H-Aib-His-D-2Nal-D-Phe-NH)-(4-pyridyl)ethane
H-Aib-Phe-D-2Nal-D-Phe-Lys-NH$_2$
2-(H-Aib-His-D-2Nal-D-Phe-NH)-(1-methyl-2-pyrrolidinyl)ethane
2-(H-Aib-His-D-2Nal-D-Phe-NH)-(4-pyridyl)ethane
H-Aib- Msψ(CH.NH)-D-2Nal-D-Phe-Lys-OH
(3-Am inomethylbenzoyl)-D-2Nal-N-Me-D-Phe-Lys-NH$_2$
H-Aib-His-D-2Nal-D-Phe-Gly-NH$_2$
H-Aib-His-D-2Nal-D-Phe-Ala-NH$_2$
H-Aib-His-D-2Nal-D-Phe-Orn-NH$_2$
(5-Aminomethylthienyl-2-carbonyl)-D-2Nal-D-Phe-Lys-NH$_2$
H-Aib-His-D-2Nal-D-Phe-D-Lys-NH$_2$
H-Aib-His-D-2Nal-D-Phe-Dab-NH$_2$
H-Aib-His-D-2Nal-D-Pheψ(CH$_2$NH)-Lys-NH$_2$
H-Aib-His-N-Me-D-2Nal-D-Phe-Lys-NH$_2$
H-Aib-His-D-2Nal-D-Phe-N-Me-Lys-NH$_2$
(3-Aminomethylthienyl-2-carbonyl)-D-2Nal-D-Phe-Lys-NH$_2$
H-Aib-His-D-2Nal-N-Me-D-Phe-Lys-NH$_2$
H-Aib-His-D-2Nal-D-Phe-Lys-N(Me)$_2$
(3R)-Piperidinecarbonyl-D-2Nal-D-Phe-Lys-NH$_2$
(3S)-Piperidinecarbonyl-D-2Nal-D-Phe-Lys-NH$_2$
(3-Aminomethylbenzoyl)-D-lNal-D-Phe-Lys-NH$_2$
H-Aib-His-D-2Nal-D-Trp-Lys-NH$_2$
(Furfuryl)-Aib-His-D-2Nal-D-Phe-Lys-NH$_2$
(2-Pyridylmethyl)-Aib-His-D-2Nal-D-Phe-Lys-NH$_2$
H-Aib-(3-aminomethylbenzoyl)-D-2Nal-D-Phe-Lys-NH$_2$
H-Aib-3Pyal-D-2Nal-D-Phe-Lys-NH$_2$
(3S)-Piperidinecarbonyl-D-2Nal-D-Phe-Lys-NH$_2$
(3R)-Piperidinecarbonyl-D-2Nal-D-Phe-Lys-NH$_2$
(2-(H-Aib-His-D-2Nal-NH)ethyl)benzene
N,N-di(2R-Hydroxypropyl)-(3-aminomethylbenzoyl)-D-2Nal-D-Phe-Lys-NH$_2$
(2R-Hydroxypropyl)-Aib-His-D-2Nal-D-Phe-Lys-NH$_2$
(3-Aminomethylbenzoyl)-D-2Nal-D-Pheψ(CH$_2$NH)Lys-NH$_2$
(3-Aminomethylbenzoyl)-N-Me-D-2Nal-D-Phe-Lys-NH$_2$
(3-Aminomethylbenzoyl)-D-2Nal-D-Phe-N-Me-Lys-NH$_2$
H-D-Thr-His-D-2Nal-D-Phe-Lys-NH$_2$
H-Aib-His-D-2Nal-N-(phenethyl)-Gly-Lys-NH$_2$
(3-Aminomethylbenzoyl)-D-2Nal-N-(phenethyl)-Gly-Lys-NH$_2$
H-Hyp-His-D-2Nal-D-Phe-Lys-NH$_2$
H-Aib-His-N-Me-D-2Nal-N-(phenethyl)-Gly-Lys-NH$_2$
H-Aib-His-N-Me-D-2Nal-N-Me-D-Phe-Lys-NH$_2$
H-Aib-His-D-2Nal-D-Pheψ(CH$_2$N(Me))Lys-NH$_2$
3-(H-Aib-His-D-2Nal-N-Me-D-Phe-NH)morpholinopropane
2-(H-Aib-His-D-2Nal-N-Me-D-Phe-NH)-(1-methyl-2-pyrrolidinyl)ethane
(3R)-Piperidinecarbonyl-N-Me-D-2Nal-N-Me-D-Phe-Lys-NH$_2$
3-((Aminomethylbenzoyl)-D-2Nal-N-Me-D-Phe-NH)morpholinopropane
2-(H-Aib-His-N-Me-D-2Nal-N-Me-D-Phe-NH)-(1-methyl-2-pyrrolidinyl)ethane
2-(3R)-Piperidinecarbonyl-N-Me-D-2Nal-N-Me-D-Phe-NH)-(1-methyl-2-pyrrolidinyl)ethane
2-(3-Aminomethylbenzoyl)-N-Me-D-2Nal-N-Me-D-Phe-NH)-(1-methyl-2-pyrrolidinyl)ethane
3-(H-Aib-His-N-Me-D-2Nal-N-Me-D-Phe-NH)morpholinopropane
3-((3R)-Piperidinecarbonyl-N-Me-D-2Nal-N-Me-D-Phe-NH)morpholinopropane
3-((3-Aminomethylbenzoyl)-N-Me-D-2Nal-N-Me-D-Phe-NH)morpholinopropane
H-Aib-His-D-2Nal-N-Me-D-Phe-Hyp-NH$_2$
2-((3-Aminomethylbenzoyl)-D-2Nal-N-Me-D-Phe-NH)-( 1-methyl-2-pyrrolidinyl)ethane
2-((3R)Piperidinecarbonyl-D-2Nal-N-Me-D-Phe-NH)-(1-methyl-2-pyrrolidinyl)ethane Abbreviations:
D-2Nal=D-2-naphthylalanine
5Apent=5-aminopentanoic acid
3Pyal=3-pyridylalanine
Aib=H-amino-isobutyric acid
5 Thial=cthienylalanine
hp he homo-phenylalanine
N-Bzl-Gly=N-benyiglycine
4 F=4-fluoro
4-OMe=4-methoxy
10 Orn=ornithine
Dab=2,4-diaminobutyric acid
Hyp=hydroxyproline
Tic=1,2,3,4-tetrahydroisoquinoline-3-carboxylic acid Compounds of formula I may be prepared by conventional methods of solution or solid phase peptide synthesis. For instance, solid phase synthesis may be carried out substantially as described by Stewart and Young, *Solid Phase Pepatide Sythesis*, 2nd. Ed., Rockford, Ill. USA, 1976. Solution peptide synthesis may for instance be carried out substantially as described by Bodansky et al., Peptide Synthesis, 2nd. Ed., New York. N.Y., USA, 1976.

Aminomethylene as a substitution of an amide bond may be introduced according to the method described by Y. Sasaki and D. H. Coy, Peptides 8(1), 1987, pp.119–121. Peptide derivatives containing a mono- or di-hexapyranose derivatised amino group may be prepared by an Amadori rearrangement substantially be the method described by R. Albert et al., *Life Sciences* 53 1993, pp.517–525. Examples of suitable mono- or di-hexapyranoses are glucose, galactose, maltose, lactose or cellobiose. Derivatives used as starting materials in the synthesis may either be obtained commercially and, when required, provided with suitable protecting groups, or starting materials used to prepare the "A" moiety in general formula I may b e prepare d by well-known methods and optionally protected in a manner known per se.

Pharmaceutically acceptable acid addition salts of compounds of formula I include those prepared by reacting the peptide with an inorganic or organic acid such as hydrochloric, hydrobromic, sulfuric, acetic, phosphoric, lactic, maleic, phthalic, citric, glutaric, gluconic, methanesulfonic, salicylic, succinic, tartaric, toluenesulfonic, trifluoroacetic, sulfamic and fumaric acid.

In another aspect, the present invention relates to a pharmaceutical composition comprising, as an active ingredient, a compound of the general formula I or a pharmaceutically acceptable salt thereof together with a pharmaceutically acceptable carrier or diluent. Pharmaceutical compositions containing a compound of the present invention may be prepared by conventional techniques, e.g. as described in *Remington's Pharmaceutical Sciences*, 1985. The compositions may appear in conventional forms, for example capsules, tablets, aerosols, solutions, suspensions or topical applications.

The pharmaceutical carrier or diluent employed may be a conventional solid or liquid carrier. Examples of solid carriers are lactose, terra alba, sucrose, cyclodextrin, talc, gelatin, agar, pectin, acacia, magnesium stearate, stearic acid or lower alkyl ethers of cellulose. Examples of liquid carriers are syrup, peanut oil, olive oil, phospholipids, fatty acids, fatty acid amines, polyoxyethylene and water.

Similarly, the carrier or diluent may include any sustained release material known in the art, such as glyceryl monostearate or glyceryl distearate, alone or mixed with a wax.

If a solid carrier is used for oral administration, the preparation may be tabletted, placed in a hard gelatin capsule in powder or pellet form or it can be in the form of a troche or lozenge. The amount of solid carrier will vary widely but will usually be from about 25 mg to about 1 g.

A typical tablet which may be prepared by conventional tabletting techniques may contain:

| Core: | |
| --- | --- |
| Active compound (as free compound or salt thereof) | 100 mg |
| Colloidal silicon dioxide (Aerosil) | 1.5 mg |
| Cellulose, microcryst. (Avicel) | 70 mg |
| Modified cellulose gum (Ac—Di—Sol) | 7.5 mg |
| Magnesium stearate | |
| Coating: | |
| HPMC approx. | 9 mg |
| *Mywacett 9–40 T approx. | 0.9 mg |

*Acylated monoglyceride used as plasticizer for film coating.

If a liquid carrier is used, the preparation may be in the form of a syrup, emulsion, soft gelatin capsule or sterile injectable liquid such as an aqueous or non-aqueous liquid suspension or solution.

For nasal administration, the preparation may contain a compound of formula I dissolved or suspended in a liquid carrier, in particular an aqueous carrier, for aerosol application. The carrier may contain additives such as solubilizing agents, e.g. propylene glycol, surfactants such as bile acid salts or polyoxyethylene higher alcohol ethers, absorption enhancers such as lecithin (phosphatidylcholine) or cyclodextrin, or preservatives such as parabenes.

Generally, the compounds of the present invention are dispensed in unit dosage form comprising 0.0001–100 mg of active ingredient together with a pharmaceutically acceptable carrier per unit dosage.

The dosage of the compounds according to this invention is suitably 1–500 mg/day, e.g. about 100 mg per dose, when administered to patients, e.g. humans, as a drug.

It has been demonstrated that compounds of the general formula I possess the ability to release endogenous growth hormone in vivo. The compounds may therefore be used in the treatment of conditions which require increased plasma growth hormone levels such as in growth hormone deficient humans or in elderly patients or livestock.

Thus, in a particular aspect, the present invention relates to a pharmaceutical composition for stimulating the release of growth hormone from the pituitary, the composition comprising, as an active ingredient, a compound of the general formula I or a pharmaceutically acceptable salt thereof together with a pharmaceutically acceptable carrier or diluent.

In a further aspect, the present invention relates to a method of stimulating the release of growth hormone from the pituitary, the method comprising administering to a subject in need thereof an effective amount of a compound of the general formula I or a pharmaceutically acceptable salt thereof.

In a still further aspect, the present invention relates to the use of a compound of the general formula I or a pharmaceutically acceptable salt thereof for the preparation of a medicament for stimulating the release of growth hormone from the pituitary.

To those skilled in the art, it is well known that the current and potential uses of growth hormone in humans are varied and multitudinous. It is anticipated that, compounds of formula I can be administered for purposes of stimulating release of growth hormone from the pituitary and would then have similar effects or uses as growth hormone itself. The uses of growth hormone may be summarized as follows: stimulation of growth hormone release in the elderly; prevention of catabolic side effects of glucocorticoids, treatment of osteoporosis, stimulation of the immune system, acceleration of wound healing, accelerating bone fracture repair, treatment of growth retardation, treating renal failure or insufficiency resulting from growth retardation, treatment of physiological short stature including growth hormone deficient children and short stature associated with chronic illness, treatment of obesity and growth retardation associated with obesity, treating growth retardation associated with the Prader-Willi syndrome and Turner's syndrome; accelerating the recovery and reducing hospitalization of burn patients; treatment of intrauterine growth retardation, skeletal dysplasia, hypercortisolism and Cushing's syndrome; induction of pulsatile growth hormone release; replacement of growth hormone in stressed patients, treatment of osteochondrodysplasias, Noonan's syndrome, schizophrenia, depressions, Alzheimer's disease, delayed wound healing and psychosocial deprivation, treatment of pulmonary dysfunction and ventilator dependency, attenuation of protein catabolic responses after major surgery, reducing cachexia and protein loss due to chronic illness such as cancer or AIDS; treatment of hyperinsulinemia including nesidioblastosis, adjuvant treatment for ovulation induction; to stimulate thymic development and prevent the age-related decline of thymic function, treatment of immunosuppressed patients, improvement in muscle strength, mobility, maintenance of skin thickness, metabolic homeostasis, renal homeostasis in the frail elderly, stimulation of osteoblasts, bone remodelling and cartilage growth, stimulation of the immune system in companion animals and treatment of disorder of aging in companion animals, growth promoter in livestock and stimulation of wool growth in sheep.

For the above indications the dosage may vary depending on the compound of formula I employed, on the mode of administration and on the therapy desired. However, generally dosage levels between 0.0001 and 100 mg/kg body weight per day may be administered to patients and animals to obtain effective release of endogenous growth hormone. Usually, dosage forms suitable for oral or nasal administration comprise from about 0.0001 mg to about 100 mg, preferably from about 0.001 mg to about 50 mg of the compounds of formula I admixed with a pharmaceutically acceptable carrier or diluent.

The compounds of formula I may be administered in pharmaceutically acceptable acid addition salt form or, where appropriate, as a alkali metal or alkaline earth metal or lower alkylammonium salt. Such salt forms are believed to exhibit approximately the same order of activity as the free base forms.

Optionally, the pharmaceutical composition of the invention may comprise a compound of formula I combined with one or more compounds exhibiting a different activity, e.g., an antibiotic or other pharmacologically active material. This might be another secretagogue, such as GHRP (1 or 6) or GHRH or an analogue thereof, growth hormone or an analogue thereof or a somatomedin such as IGF-1 or IGF-2.

The route of administration may be any route which effectively transports the active compound to the appropriate or desired site of action, such as oral, nasal or parenteral, the oral route being preferred.

Apart from the pharmaceutical use of the compounds of formula I, they may be useful in vitro tools for investigating the regulation of growth hormone release.

The compounds of formula I may also be useful in vivo tools for evaluating the growth hormone releasing capability of the pituitary. For example, serum samples taken before and after administration of these compounds to humans can be assayed for growth hormone. Comparison of the growth hormone in each serum sample would directly determine the ability of the patient's pituitary to release growth hormone.

Compounds of formula I may be administered to commercially important animals to increase their rate and extent of growth, and to increase milk production.

Pharmacological Methods

Compounds of formula I may be evaluated in vitro for their efficacy and potency to release growth hormone in primary rat somatotrophs.

Rat primary somatotrophs may be prepared essentially as described previously (Chen t al., Endocrinology 1991, 129, 3337–3342 and Chen et al., Endocrinology 1989, 124, 2791–2798). Briefly, rats are killed by decapitation. The pituitary is quickly removed. H pituitaries are digested with 0.2% collagenase and 0.2% hyalurinidase in Hanks balanced salt solution. The cells are resuspended in Dulbecco's Modified Eagle's medium containing 0.37% NaHCO3, 10% horse serum, 2.5% fetal calf serum, 1% nonessential amino acids, 1% glutamine and 1% penicillin/streptomycin and adjusted to 1.5×105 cells/ml. One ml of this suspension is placed in each well of 24-well trays and left for 2–3 days before release experiments are performed.

On day one of the experiments, cells are washed twice with the above medium containing 25 mM HEPES, pH 7.4. Growth hormone release initiated by addition of medium containing 25 mM HEPES and test compound. Incubation is carried out for 15 minutes at 37° C. After incubation growth hormone released to the medium is measured by a standard RIA.

Compounds of formula I may be evaluated for their in vivo effects on growth hormone release in pentobarbital anaesthetized female rats as described previously (Bercu et al. Endocrinology 1991, 129, 2592–2598). Briefly, adult male Sprague-Dawley rats are anesthetized with pentobarbital 50 mg/kg ip. After the rats had been fully anaesthesized the rats are implanted with a tracheal cannula and catheters in the carotid artery and the jugular vein. After a 15 minute recovery, a blood sample is taken at time 0. The pituitary secretagogues are administered iv and artery blood samples are put on ice for 15 minutes and then centrifuged for 2 minutes at 12,000 ×g. The serum is decanted and amount of growth hormone determined using a standard RIA.

The invention is further illustrated in the following examples which are not in any way intended to limit the scope of the invention as claimed.

The abbreviations used throughout this description and examples indicate the following structures:

Abbreviations for non-natural amino acid residues:

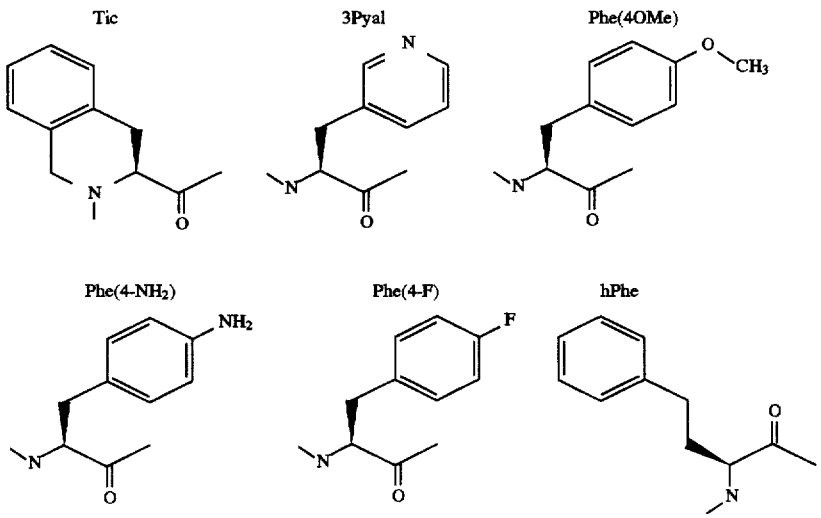

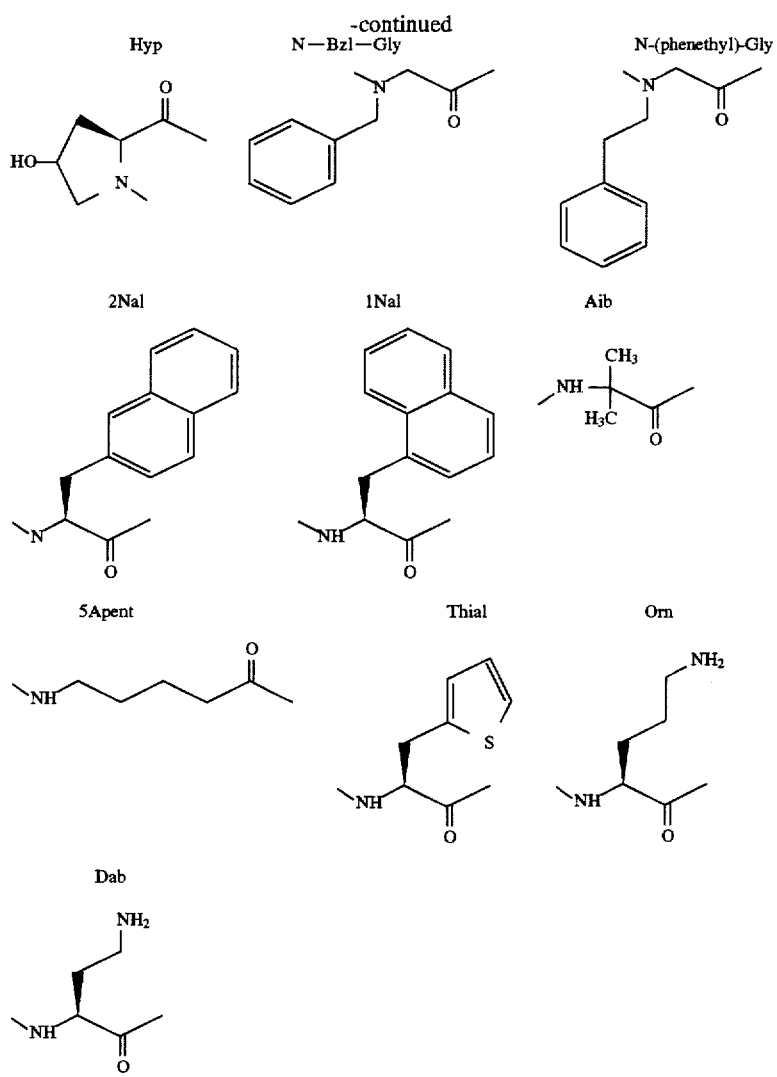
Abbreviations used for peptide bond substitutions:
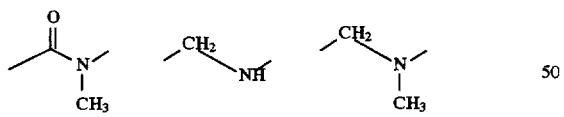
Abbreviations used for protecting groups:

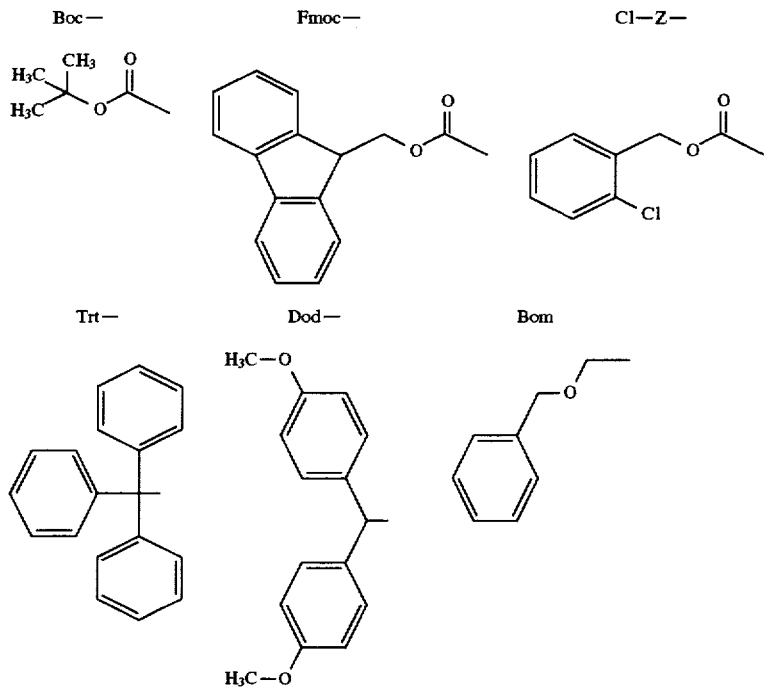

The compounds prepared in the following examples were all isolated as the trifluoroacetic acid (TFA) salts.

EXAMPLE 1

H-Ala-His-D-2Nal-D-Trp-Lys-NH$_2$

The title peptide was synthesized according to the Fmoc strategy on an Applied Biosystems 431A peptide synthesizer in 0.22 mmol scale using the manufacturer supplied Fast-Moc UV protocols which employ HBTU ( 2-(1H-Benzotriazol-1-yl-)-1,1,3,3 tetramethyluronium hexafluorophosphate) mediated couplings in NMP (N-methyl pyrrolidone) and UV monitoring of the deprotection of the Fmoc protection group. The starting resin used for the synthesis was 559 mg 4-(1, 2', 4'-dimethoxyphenyl)-(Fmoc-amino)methyl)-phenoxy resin ( Novabiochem, Bad Soden, Germany. cat. #: 01-64-0013) with a substitution capacity of 0.39 mmol/g. The protected amino acid derivatives used were Fmoc-Lys(Boc)-OH, Fmoc-D-Trp-OH, Fmoc-2Nal-OH, Fmoc-His(Trt) and Fmoc-Ala-OH.

The peptide was cleaved from 434 mg of the peptide resin by stirring for 180 min at room temperature with a mixture of 4 ml TFA (trifluoroacetic acid), 300 mg phenol, 100 µl ethanedithiol, 200 µl thioanisole and 200 µl H$_2$O. The cleavage mixture was filtered and the filtrate was concentrated to 1 ml by a stream of nitrogen. The crude peptide was precipitated from this oil with 45 ml diethyl ether and washed 3 times with 50 ml diethyl ether.

The crude peptide was dryed and purified by semipreparative HPLC on a 20 mm x 250 mm column packed with 7µC-18 silica which was preequilibrated with 15% CH$_3$CN in 0.05M (NH$_4$)$_2$SO$_4$, which was adjusted to pH 2.5 with 4M H$_2$SO$_4$. The crude peptide was dissolved in 2 ml 70% CH$_3$CN / 0.1% TFA in H$_2$O and diluted to 100 ml with H$_2$O.

This solution was divided into two equal portions and each of them were injected on the column in two separate runs. The column was eluted with a gradient of 15%–25% CH$_3$CN in 0.05M (NH$_2$),SO$_4$, pH 2.5 at 10 ml/min during 47 min at 40° C. The peptide containing fractions were collected, diluted with 3 volumes of H M0 and applied to a SEP-PAK® C18 silica cartridge (Waters part. #:51910) which was equilibrated with 0.1% TFA. The peptide was eluted from the SEP-PAK® C18 silica 5 cartridge with 70% CH$_3$CN 0.1% T2A and isolated from the eluate by lyophilisation after dilution with water. A yield of 19.0 mg was obtained.

The final product obtained was characterised by analytical RP-HPLC (retention time) and by Plasma desorption mass spectrometry (molecular mass). Mass spectrometry agreed with the expected structure within the experimental error of the method (mass spectrometry±0.9 amu).

The RP-HPLC analysis was performed using UV detection at 214 nm and a Vydac 2 18TP54 4.6 mm×250 mm 5µC-18 silica column (The Separations Group, Hesperia) which was eluted at 1ml/min at 42° C. Two different elution conditions were used:

A1: The column was equilibrated with 5% CH$_3$CN in a buffer consisting of 0.1M (NH$_2$),SO$_4$ , Which was adjusted to pH 2.5 with 4 M H$_2$SO$_4$ and eluted by a gradient of 5% to 60% CH$_3$CN in the same buffer during 50 min.

B1: The column was equilibrated with 5% CH$_3$CN i 0.1% T iA i H w t an d eluted by a gradient of 5% CH$_3$CN/0.1% TFA/H$_2$O to 60% CH$_3$CN/0.1% TFA/H$_2$O during 50 min.

The retention time using elution conditions Al and Bi was found to be 17.88 m i and 20.15 min, respectively.

EXAMPLE 2

H-Ala-His-D-2Nal-D-Phe-Lys-OH

The title peptide was synthesized using a procedure similar to the one described in example 1, with the exception that 450 mg Fmoc-Lys(Boc)-Wang resin (Novabiochem, Bad Soden, Germany. cat. # 04–12–2014) with a substitution capacity of 0.49 mmol/g was used as the starting resin. Upon cleavage of 560 mg peptide resin and purification of ½ of the resulting crude product as described in example 1. a yield of 25.9 mg was obtained.

The final product was characterised as described in Example 1. The retention time using elution conditions Al and B i was found to be 18.30 min and 20.15 min. respectively.

EXAMPLE 3

5-(H-Ala-His-D-2Nal-D-Phe-NH)aminopentane

The peptide resin H-Ala-His(Trt)-D-2Nal-D-Phe- Sasrin resin was synthesized using a procedure similar to the one described in Example 1. with the exception that 262 mg Sasrin resin (2-Methoxy-4-alkoxybenzyl alcohol resin) (Bachem. Bubendorf. Switzerland cat. # D-1295) with a substitution capacity of 0.96 mmol/g was used and the protocol used for coupling of the first amino acid residue to the resin was a 4-dimethylaminopyridine catalysed coupling of the preformed symmetrical anhydride followed by capping of residual —OH groups on the resin with benzoic anhydride.

The partially protected peptide 5-(H-Ala-His(Trt)-D-2Nal-D-Phe-NH)aminopentane was cleaved from 56 mg of the H-Ala-His(Trt)-D-2Nal-D-Phe- Sasrin resin by stirring for 20 h at room temperature with 0.5 ml of 1.5-diaminopentane. The spent resin was filtered off and extracted with 1 ml DMF. The combined filtrate and extract was slowly added to a mixture of 2.5 ml $CH_3CN$ and 10 ml 1M hydrochloric acid under stirring and after dilution to 50 ml with 25% $CH_3CN$ the mixture was left at 4° C. for 100 h (for cleavage of the trityl protection on the histidine). The mixture was then diluted to 200 ml with $H_2O$ and filtered.

The crude peptide was purified by semipreparative HPLC by direct injection on the column of ½ of this filtrate using a procedure similar to that described in example 1. The yield was 4.5 mg.

The final product was characterised as described in Example 1. The retention time using elution conditions A land B lwas found to be 18.43 min and 20.75 min. respectively.

EXAMPLE 4

(2S)-(H-Ala-His-D-2Nal-D-Phe-NH)-6-aminohexanol

The peptide resin H-Ala-His(Trt)-D-2Nal-D-Phe-Lys (Boc)-Sasrin resin was synthesized using a procedure similar to the one described in Example 3 from a Sasrin resin with a substitution capacity of 0.96 mmol/g.

The partially protected peptide (2S)-(H-Ala-His(Trt)-D-2Nal-D-Phe-NH)-6-aminohexanol was cleaved from 200 mg of the H-Ala-His(Trt)-D-2Nal-D-Phe-Lys(Boc)-Sasrin resin by stirring the peptide resin for 20 h at room temperature with a mixture of 1.2 ml THF (tetrahydrofuran) 0.2 ml ethanol, 23 mg LiBr and 10 mg $NaBH_4$. Then 200 µl $H_2O$, 200 µl acetic acid and 4 ml ethanol was added. The resin beads were removed by filtration and the filtrate was diluted with 50 ml $H_2O$ and lyophilized. The resulting powder was subjected to TFA cleavage and purification as described in example 1. The purification had to be repeated in order to obtain a sufficiently pure product. A yield of 5.8 mg was obtained.

The final product was characterised as described in Example 1. The retention time using elution conditions A1 and B1 was found to be 17.82 min and 20.02 min respectively.

EXAMPLE 5

H-Ala-Hisψ(CH$_2$NH)D-2Nal-D-Phe-Lys-NH$_2$

The peptide resin H-D-2Nal-D-Phe-Lys-(Boc)Resin was synthesized using a procedure similar to the one described in Example 1 starting from 556 mg 4-((2',4'-dimethoxyphenyl)-(Fmoc-amino)methyl)-phenoxy resin resin ( Novabiochem AG Switzerland. cat. #: 01-64-0013) having a substitution capacity of 0.34 mmol/g . The following protected amino acid derivatives were used: Fmoc-Lys(Boc)-OH. Fmoc-D-Phe-OH and Fmoc-2Nal-OH.

The -CH$_2$NH- peptide bond isostere was introduced according to Sasaki. Y. and Coy. D. H.. PEPTIDES 8(1) 119–121. 1987.

Fmoc-His(Trt)-aldehyde was prepared from 820 mg of the corresponding N,O -dimethyl hydroxamate according to Fehrentz. J. -A. and Castro. B.. SYNTHESIS 676–678. 1983. The crude aldehyde was dissolved in 8 ml DMF and divided into two portions. The first portion was added to a stirred slurry of 610 mg of H-D-2Nal-D-Phe-Lys-Resin in 10 ml 1% acetic acid in DMF at room temperature. Then 57 mg NaCNBH$_3$ (85% pure) dissolved in 1 ml DMF was added and stirring was continued for 60 min. After this the peptide resin was isolated by filtration and washed with 1% acetic acid in DMF. The peptide resin was again suspended in 10 ml 1% acetic acid in DMF and the second portion of the Fmoc-His(Trt)-aldehyde was added. Again 57 mg NaCNBH$_3$ (85% pure) dissolved in 1 ml DMF was added at room temperature and the mixture was stirred for 18 h.

After this reductive alkylation step, the peptide resin was isolated by filtration and washed with 1% acetic acid in DMF and the chain elongation was completed using the peptide synthesizer according to the above described procedures using the protected amino acid derivative Fmoc-Ala-OH.

The peptide was cleaved from 550 mg of the peptide resin and the crude peptide was purified by semipreparative HPLC using a procedure similar to that described in Example 1. A yield of 11.3 mg was obtained.

The final product was characterised as described in Example 1. The retention time using elution conditions Al and B i was found to be 13.35 min and 17.38 min respectively.

EXAMPLE 6

(n-Propyl)-His-D-2Nal-D-Phe-Lys-NH$_2$ and (n-propyl)$_2$-His-D-2-Nal-D-Phe-Lys-NH$_2$ The peptide resin H-His(Trt)-D-2Nal-D-Phe-Lys(Boc)-Resin was synthesized using a procedure similar to the one described in Example 1 starting from 4-((2'.4'-dimethoxyphenyl)-(Fmoc-amino)methyl)-phenoxy resin resin ( Novabiochem AG Switzerland. cat. #: 01-64-0013 ) having a substitution capacity of 0.34 mmol/g. The protected amino acid derivatives used were Fmoc-Lys(Boc)-OH, Fmoc-D-Phe-OH, Fmoc-2Nal-OH and Fmoc-His(Trt)-OH.

13 µl n-propanal was added to a stirred slurry of 150 mg of H-His(Trt)-D-2Nal-D-Phe-Lys-Resin in 3.3 ml 1% acetic acid in DMF at room temperature. Then 16.8 mg NaCNBH$_3$ (85% pure) dissolved in 0.5 ml DMF was added and stirring was continued for 6 h. After this reductive alkylation step, the peptide resin was isolated and washed on a filter funnel with DMF and $CH_2Cl_2$ and then dried in vac.

The two resulting peptide resins were mixed and a mixture of unalkylated, mono-n propyl and di-n-propyl peptide was cleaved from the resulting 300 mg peptide resin. The peptides were separated and purified by semipreparative HPLC using a procedure similar to that described in example 1. A yield of 6.54 mg of n-propyl-His-D-2Nal-D-Phe-Lys-NH$_2$ and 5.59 mg of (n-propyl)$_2$-His-D-2Nal-D-Phe-Lys-NH$_2$ was obtained.

The final products were characterised as described in example 1. For (n-propyl)-His-D-2Nal-D-Phe-Lys-NH$_2$ the retention time using elution conditions A1 and B1 was found to be 16.45 min and 19.92 min, respectively.

EXAMPLE 7

H-Ala-Tic-D-2Nal-D-Phe-Lys-NH$_2$

Starting from 620 mg 4-methyl BHA resin (Bissendorf Biochemicals, Hannover, Germany, cat. #: RMIS50) having a substitution capacity of 0.72 mmol/g the peptide was synthesized according to the Boc strategy on an Applied Biosystems 430A peptide synthesizer using the manufacturer supplied 0.5 mmol scale single coupling protocols which employ single couplings with preformed symmetrical anhydrides in DMF. The protocols were adjusted to 60 min coupling time. A double coupling with 2×60 min coupling time was used for the N-terminal Ala. The protected amino acid derivatives used for the synthesis was Boc-Lys(2-chloro-Z)-OH, Boc-D-Phe-OH, Boc-D-2Nal-OH, Boc-Tic-OH and Boc-Ala-OH.

The peptide was cleaved from 486 mg of the peptide resin by stirring it for 75 min at 0° C. with a mixture of 4.5 ml HF and 500, µl m-cresol. The HF was evaporated at 0° C. by a stream of nitrogen. The peptide was precipitated from the remaining oil together with the spend resin with 50 ml diethyl ether and washed 2 times with 50 ml diethyl ether. After drying the peptide was extracted precipitate with 10 ml H$_2$O containing 4 drops of acetic acid. The extract was diluted to 100 ml H$_2$O.

The crude peptide was purified from 2×18 ml of the diluted extract by two runs of semipreparative HPLC using a procedure similar to that described in example 1. The yield was 17.3 mg.

The final product was characterised as described in example 1.

RP-HPLC analysis using conditions A1 and B1 gave the retention times 27.37 min and 29.50 min respectively.

EXAMPLE 8

(2R)-(H-Ala-His-D-2Nal-NH)-3-phenylpropylamine

The Fmoc group was removed by treatment with 20% piperidine in NMP for 20 min from 580 mg 4-((2',4'-dimethoxyphenyl)-(Fmoc-amino)methyl)-phenoxy resin resin (Novabiochem AG Switzerland, cat. #: 01-64-0013) having a substitution capacity of 0.43 mmol / g. The resin was washed with DMF and with CH$_2$Cl$_2$ and alkylated with Fmoc-D-Phe-aldehyde using a reductive alkylation procedure described in example 5.

After this, the peptide resin was isolated by filtration and washed with 1% acetic acid in DMF on a filter funnel and the chain elongation was completed using the peptide synthesizer as described in example 1, using the protected amino acid derivatives Fmoc-D-2Nal-OH, Fmoc-His(Trt)-OH and Fmoc-Ala-OH.

The peptide was cleaved from 301 mg of the peptide resin and the crude peptide was purified by semipreparative HPLC using a procedure similar to that described in example 1. A yield of 23.92 mg was obtained.

The final product was characterised as described in Example 1. The retention time using elution conditions A1 and B1 was found to be 19.33 min and 21.77 min respectively.

| Ex. | Peptide | Prepared using a procedure similar to Example | RP-HPLC retention time for condition A1 (Ex. 1) | RP-HPLC retention time for condition B1 (Ex. 1) |
|---|---|---|---|---|
| 9 | H—Ala—His—D—Phe—D—Phe—Lys—NH$_2$ | 1 | 12.53 | 15.43 |
| 10 | H—Ala—Phe—D-2Nal-D—Phe—Lys—NH$_2$ | 1 | 28.13 | 29.62 |
| 11 | H—His—D-2Nal-D—Phe—Lys—NH$_2$ | 1 | 18.02 | 20.15 |
| 12 | H—Ala—His—D-2Nal-D—Phe—Phe—NH$_2$ | 1 | 28.48 | 29.48 |
| 13 | H—Ala—His—D-2Nal-D—Phe—D—Phe—NH$_2$ | 1 | 26.65 | 27.75 |
| 14 | H—Ala—His—D-2Nal-Phe—Lys—NH$_2$ | 1 | 21.85 | 23.12 |
| 15 | (3-(4-Imidazolyl)propionyl)-D-2Nal-D—Phe—Lys—NH$_2$ | 1 | 20.7 | |
| 16 | (Propionyl)-His—D-2Nal-D—Phe—Lys—NH$_2$ | 1 | 22.2 | 23.77 |
| 17 | H—Ala—His—D-2Nal-D—Phe—NH$_2$ | 1 | 21.7 | 23.08 |
| 18 | (H—Ala—His—D-2Nal-D—Phe—NH)hexane | 3 | 34.11 | 35.78 |
| 19 | H—Ala—His—D—Trp—D—Phe—Lys—NH$_2$ | 1 | 14.52 | 16.7 |
| 20 | H—Ala—Ala—D-2Nal-D—Phe—Lys—NH$_2$ | 1 | 21.97 | 23.23 |
| 21 | ((Propionyl)-His—D-2Nal-D—Phe—NH)hexane | 3 | 37.17 | 39.47 |
| 22 | 6-(H—Ala—His—D-2Nal-D—Phe—NH)hexylamine | 3 | 19.3 | 21.57 |
| 23 | H—D-2Nal-D—Phe—Lys—NH$_2$ | 1 | 15.88 | 18.25 |
| 24 | (5-Aminopentanoyl)—His—D-2Nal-D—Phe—Lys—NH$_2$ | 1 | 17.8 | 19.98 |
| 25 | H—D—Lys—D-2Nal-D—Phe—Lys—NH$_2$ | 1 | 17.07 | 19.62 |
| 26 | H—Ala—His—D-2Nal-D—Tic—Lys—NH$_2$ | 1 | 19.12 | 20.78 |
| 27 | H—D—Lys—Phe-2Nal-D—His—D—Ala—NH$_2$ | 1 | 18.15 | 20.48 |
| 28 | (5—Aminopentanoyl)—D-2Nal-D—Phe—Lys—NH$_2$ | 1 | 20.67 | 22.45 |

-continued

| Ex. | Peptide | Prepared using a procedure similar to Example | RP-HPLC retention time for condition A1 (Ex. 1) | RP-HPLC retention time for condition B1 (Ex. 1) |
|---|---|---|---|---|
| 29 | H—D—Ala—D-2Nal-D—Phe—Lys—NH$_2$ | 1 | 19.57 | 21.53 |
| 30 | (Propionyl)—D-2Nal-D—Phe—Lys—NH$_2$ | 1 | 26.7 | 27.92 |
| 31 | H—D—Ala—His—D-2Nal-D—Phe—Lys—NH$_2$ | 1 | 17.83 | 20.3 |
| 32 | H—Ala-3-Pyal—D-2Nal-D—Phe—Lys—NH$_2$ | 1 | 18.15 | 20.18 |
| 33 | (n-Butyl)-Ala—His—D-2Nal-D—Phe—Lys—NH$_2$ | 6 | 19.55 | — |
| 34 | (n-Octyl)-Ala—His—D-2Nal-D—Phe—Lys—NH$_2$ | 6 | 27.88 | 24.52 |
| 35 | H—Ala—His—D-2Nal-D—Phe$\psi$(CH$_2$NH)Lys—NH$_2$ | 5 | 17.97 | 20.83 |
| 36 | (3-Aminomethylbenzoyl)-D-2Nal-D—Phe—Lys—NH$_2$ | 1 | 22.42 | 24.13 |
| 37 | (3-Aminophenylacetyl)-D-2Nal-D—Phe—Lys—NH$_2$ | 1 | 23.62 | 23.97 |
| 38 | ((4-Imidazolyl)acetyl)-D-2Nal-D—Phe—Lys—NH$_2$ | 1 | 20.42 | 22.22 |
| 39 | (3-(4-Imidazolyl)acryloyl)-D-2Nal-D—Phe—Lys—NH$_2$ | 1 | 21.25 | 23.32 |
| 40 | (4-Aminophenylacetyl)-D-2Nal-D—Phe—Lys—NH$_2$ | 1 | 22.45 | — |
| 41 | (Trans-4-aminomethylcyclohexanoyl)-D-2Nal-D—Phe—Lys—NH$_2$ | 1 | 22.07 | 23.67 |
| 42 | 2-(H—Ala—His—D-2Nal-D—Phe—NH)-ethylamine | 3 | 18.6 | 20.25 |
| 43 | (2-(H—Ala—His—D-2Nal-D—Phe—NH)ethyl)benzene | 3 | 30.18 | 32.18 |
| 44 | 4-((H—Ala—His—D-2Nal-D—Phe—NH)methyl)benzylamine | 3 | 19.63 | 21.55 |
| 45 | (2R)-(H—Ala—His—D-2Nal-NH)-3-phenylpropylamine | 4 | 21.55 | 23.57 |
| 46 | 2-(H—Ala—His—D-2Nal-NH)ethylamine | 3 | 25.52 | — |
| 47 | H—D—Phe—Ala—D-2Nal-D—Phe—Lys—NH$_2$ | 1 | 27.82 | 29.43 |
| 48 | H—Ala—D—Phe—D-2Nal-D—Phe—Lys—NH$_2$ | 1 | 25.62 | 27.22 |
| 49 | H—Ala—(2-aminobenzoyl)-D-2Nal-D—Phe—Lys—NH$_2$ | 7 | 26.42 | 24.93 |
| 50 | H—Aib—His—D-2Nal-D—Phe—Lys—NH$_2$ | 1 | 17.42 | 20.13 |
| 51 | H—Ala—His—D-1Nal-D—Phe—Lys—NH$_2$ | 1 | 17.55 | 19.8 |
| 52 | H—Tyr—Ala—His—D-2Nal-D—Phe—Lys—NH$_2$ | 1 | 19.9 | 21.22 |
| 53 | (Piperidine-4-carbonyl)-D-2Nal-D—Phe—Lys—NH$_2$ | 1 | 20.4 | 22.32 |
| 54 | H—Ala—Phe(4-NH$_2$)—D-2Nal-D—Phe—Lys—NH$_2$ | 1 | 19.20 | — |

EXAMPLE 55

((Propionyl)-D-2Nal-D-Phe-NH)hexane

The peptide resin (Propionyl)-D-2Nal-D-Phe-Sasrin resin was synthesized using a procedure similar to the one described in Example 3 from a Sasrin resin with a substitution capacity of 0.96 mmol/g.

105 mg of the resulting peptide resin was subjected to ammonolysis.

The peptide ((Propionyl)-D-2Nal-D-Phe-NH)hexane was cleaved from 105 mg of the Propionyl-D-2Nal-D-Phe-Sasrin resin by stirring for 20 h at room temperature with 1 ml of n-hexylamine. The spent resin was filtered off and extracted with 1 ml DMF. The combined filtrate and extract was slowly added to 8 ml 1 M hydrochloric acid under stirring. The resulting precipitate was redissolved by addition of approx. 70 ml CH$_3$CN and was then reprecipitated by addition of 20 ml H$_2$O. The precipitate was filtered off, washed with H$_2$O and dried. The yield was 12 mg.

This product was characterised as described in Example 1. with the exception that only one HPLC analysis using conditions similar to B1 with the exception that a gradient of 0.1% TFA / H$_2$O to 90% CH$_3$CN / 0.1% TFA / H$_2$O during 50 min. was used. The retention time was found to be 35.73 min.

EXAMPLE 56

(3-Methylaminomethylbenzoyl)-D-2Nal-D-Phe-Lys-NH$_2$

The peptide resin (3-Aminomethylbenzoyl)-D-2Nal-D-Phe-Lys(Cl-Z)-MBHA resin was synthesized using a procedure similar to the one described in Example 7 from a MBHA resin with a substitution capacity of 0.72 mmol/g.

The resulting peptide resin was methylated according to Kaljuste, K. and Undén, A., Int. J. Peptide Protein Res. 42 118–124. 1993. 300 mg resin was stirred for 2 h with a mixture of 8 ml DCM, 150 µl DIEA (diethylisopropylamine)and 39mg 4,4'-dimethoxydityl chloride (DOD-Cl) and then isolated by filtration and washed with DCM and with DMF. The DOD protected peptide resin was then stirred with 18 ml of a 3.7% formaldehyde solution in DMF, 0.18 ml acetic acid and 180 mg NaCNBH$_3$ was then added and stirring was continued for 18 h. The resin was isolated by filtration and washed with DMF and with DCM. The DOD protection was then removed by treatment with 2×3 ml DCM/TFA 1:1 for 5 min+30 min respectively and the peptide resin was washed with DCM and then dried in vacuum.

The resulting N-methylated peptide was cleaved from 370 mg of the resulting resin using a procedure similar to that described in example 7 and it was purified and characterized as described in example 1. The yield was 17.3 mg.

RP-HPLC analysis using conditions A1 and B1 gave the retention times of 22.83 min and 24.60 min respectively.

EXAMPLE 57

(3-Dimethylaminomethylbenzoyl)-D-2Nal-D-Phe-Lys-$NH_2$

The peptide resin (3-Aminomethylbenzoyl)-D-2Nal-D-Phe-Lys(Cl-Z)-MBHA resin was synthesized using a procedure similar to the one described in Example 7 from a MBHA resin with a substitution capacity of 0.72 mmol/g.

650 mg of the resulting peptide resin was then stirred with 20 ml 1% acetic acid in DMF and 45 μl of a 3.7% formaldehyde solution in DMF. 55 mg $NaCNBH_3$ (85%) was then added and stirring was continued for 18 h. The resin was isolated by filtration and washed with DMF, DCM/MeOH 6:4 and with DCM.

The resulting mixture of N,N-di-methylated peptides was cleaved from 631 mg of the resulting resin using a procedure similar to that described in example 7 and it was purified and characterized as described in example 1. The yield was 8.58 mg.

RP-HPLC analysis using conditions A1 and B1 gave the retention times of 31.58 min and 33.00 min respectively.

EXAMPLE 58

(3-Amino-3-methylbutanoyl)-D-2Nal-D-Phe-Lys-$NH_2$

The peptide resin H-D-2Nal-D-Phe-Lys(Boc)-Rink resin was synthesized using a procedure similar to the one described in Example 1 from 2 g 4-((2',4'-dimethoxyphenyl) -(Fmoc-amino)methyl)-phenoxy resin (Rink resin) (Novabiochem, Bad Soden, Germany. cat. #: 01-64-0013) with a substitution capacity of 0.39 mmol/g.

500 mg of the resulting peptide resin (0.15 mmol) was suspended in 4 ml DCM/MeOH 1:1. 42 μl triethylamine (0.3 mmol) was added and after cooling to 0° C., 31 mg (0.158 mmol) of 2,2-dimethyl-4-oxo-azetidine-1-sulfonylchloride was added under stirring. Stirring was continued 20 min at 0° C. and 90 min at room temperature. After washing the resin with DCM/MeOH 6:4 and drying in vacuum, the crude peptide was cleaved from the resin and purified using procedures similar to those described in example 1. The yield was 41.81 mg.

RP-HPLC analysis using conditions A1 and B1 gave the retention times of 21.35 min and 22.95 min respectively.

EXAMPLE 59

(2S)-((3-Aminomethylbenzoyl)ψ($CH_2$NH)D-2Nal-D-Phe-NH)-6-aminohexanol

The peptide resin H-D-2Nal-D-Phe-Lys(Boc)- Sasrin resin was synthesized using a procedure similar to the one described in Example 3 from 980 mg Sasrin resin with a substitution capacity of 0.87 mmol/g.

1.4 g of this resin was reductively alkylated with Boc-3-aminomethyl benzaldehyde and the peptide was cleaved from 1.0 g of the resulting resin and half of the crude product was purified the using procedures similar to those described in example 5. The yield was 18.46 mg.

RP-HPLC analysis using conditions A1 and B1 gave the retention times of 14.78 min and 17.40 min respectively.

EXAMPLE 60

(2-Aminomethylbenzoyl)-D-2Nal-D-Phe-Lys-$NH_2$

The peptide resin H-D-2Nal-D-Phe-Lys(Boc)-Rink resin was synthesized using a procedure similar to the one described in Example 1 from 2 g 4-((2',4'-dimethoxyphenyl) -(Fmoc-amino)methyl)-phenoxy resin (Rink resin) (Novabiochem, Bad Soden, Germany. cat. #: 01-64-0013) with a substitution capacity of 0.39 mmol/g.

300 mg of the resulting peptide resin (0.096 mmol) was stirred 18 h in 10 ml DMF with 54 mg phthaloyl-2-aminomethyl-benzoic acid (0.192 mmol), 182 mg HBTU (0.480 mmol)and 164 μl DIEA (0.96 mmol).

After washing the resin with DMF, DCM/MeOH 6:4 and DCM and drying in vacuum (Phthaloyl-2-aminomethylbenzoyl)-D-2Nal-D-Phe-Lys-$NH_2$ was cleaved from 290 mg of the peptide resin by stirring for 180 min at room temperature with a mixture of 3 ml TFA, 225 mg phenol, 75 μl ethanedithiol, 150 μl thioanisole and 150 =82 1 $H_2O$. The cleavage mixture was filtered, the remaining resin washed with 1 ml TFA and the filtrate was concentrated to approximately 1 ml by a stream of nitrogen. The crude peptide was precipitated from this oil with 50 ml diethyl ether and washed 3 times with 50 ml diethyl ether. The precipitate was then dissolved in 50 ml $H_2O$ and lyophilized. The resulting powder was then stirred with 0.5 ml hydrazine hydrate in 5 ml ethanol for 6 h at 70 C. and then diluted with 50 ml $H_2O$ and lyophilized.

The lyophilized product was dissolved by addition of 2 ml acetic acid, 2 ml ethanol and 100 ml $H_2O$ and purified using procedures similar to those described in example 1. The yield was 9.43 mg RP-HPLC analysis using conditions A1 and B1 gave the retention times of 23.22 min and 25.05 min respectively.

EXAMPLE 61

H-Aib-Hisψ($CH_2$NH)D-2Nal-D-Phe-Lys-OH

The peptide was synthesized using a procedure similar to the one described in example 5. with the exception that 1050 mg Sasrin resin (2-Methoxy-4-alkoxybenzyl alcohol resin) (Bachem, Bubendorf, Switzerland cat. # D-1295) with a substitution capacity of 0.87 mmol/g was used and the protocol used for coupling the first amino acid residue to the resin was a 4-dimethylaminopyridine catalysed coupling of the preformed symmetrical anhydride followed by capping of residual —OH groups on the resin with benzoic anhydride. Upon cleavage of 752 mg peptide resin and purification of 7/10 of the resulting crude product as described in example 1, a yield of 36.76 mg was obtained.

The final product was characterised as described in Example 1. The retention time using elution conditions A1 and B1 was found to be 13.90 min and 17.42 min, respectively.

EXAMPLE 62

H-Aib-His-N-Me-D-2Nal-D-Phe-Lys-$NH_2$

The peptide resin H-N-Me-D-2Nal-D-Phe-Lys(Cl-Z)-MBHA resin was synthesized using a procedure similar to the one described in Example 56 from a MBHA resin with a substitution capacity of 0.72 mmol/g. 458 mg of this resin was then used for synthesis of H-Aib-His(Bom)-N-Me-D-2Nal-D-Phe-Lys(Cl-Z)-MBHA by coupling with Boc-His (Bom)-OH and Boc-Aib-OH. The N-methylated peptide was then cleaved from 469 mg of the resulting resin and ½ of the crude peptide was purified and characterized as described in example 7. The yield was 23.5 mg.

RP-HPLC analysis using conditions A1 and B1 gave the retention times of 17.62 min and 19.95 min respectively.

EXAMPLE 63

(Furfuryl)-Aib-His-D-2Nal-D-Phe-Lys-NH$_2$

The peptide resin H-Aib-His(Trt)-D-2Nal-D-Phe-Lys (Boc)-Rink resin was synthesized using a procedure similar to the one described in Example 1 from 4-((2,4'-4'-dimethoxyphenyl)-(Fmoc-amino)methyl)-phenoxy resin (Rink resin) ( Novabiochem, Bad Soden, Germany. cat. #: 01–64–0013) with a substitution capacity of 0.43 mmol/g.

300 mg of the resulting peptide resin was then stirred with 5 ml 1% acetic acid in DMF and 410 µl of furan-2-aldehyde. 231 mg NaCNBH$_3$ (85%) was added after 15 min and after 180 min. Stirring was continued for 18h. The resin was isolated by filtration and washed with DMF, DCM/MeOH 6:4 and with DCM.

The N-alkylated peptide was cleaved from 319 mg of the resulting resin, purified and characterized as described in example 1. The yield was 44.8 mg.

RP-HPLC analysis using conditions A1 and B1 gave the retention times of 19.45 min and 22.23 min respectively.

EXAMPLE 64

N,N-di-(2R-Hydroxy-propyl)-3-aminomethylbenzoyl)-D-2Nal-D-Phe-Lys-NH$_2$

The peptide resin (3-aminomethylbenzoyl)-D-2Nal-D-Phe-Lys(CI-Z)-MBHA resin was synthesized using a procedure similar to the one described in Example 7 from 4-methyl benzhydrylamine (MBHA) resin (Bissendorf Biochemicals, Hannover, Germany. cat. #: RMIS50) having a substitution capacity of 0.72 mmol/g. 500 mg of the resulting peptide resin was then stirred with 12.5 ml 1% acetic acid in DMF and 410 µl of 2(R)-(tetrahydropyran-2 (R,S)-yloxy)propanal. 213 mg NaCNBH$_3$ (85%) was added after 5 min. Stirring was continued for 18h. The resin was isolated by filtration and washed with DMF, DCM/MeOH 6:4 and with DCM.

The N-di-alkylated peptide was cleaved from 490 mg of the resulting resin, purified and characterized as described in example 7. The yield was 20.72 mg.

RP-PLC analysis using conditions A1 and B1 gave the retention times of 23.40 m i 25.33 min respectively.

EXAMPLE 65 - 110

| Ex. | Peptide | Prepared using a procedure similar to example no. | RP-HPLC retention time for condition A1 (Ex. 1) | RP-HPLC retention time for condition B1 (Ex. 1) |
|---|---|---|---|---|
| 65 | H—Ala—N—Me—(2-aminobenzoyl)—D-2Nal-D—Phe—Lys—NH$_2$ | 7 | 24.47 | 26.27 |
| 66 | (4-Aminomethylbenzoyl)-D-2Nal-D—Phe—Lys—NH$_2$ | 1 | 22.22 | 23.5 |
| 67 | H—His—Ala—D-2Nal-D—Phe—Lys—NH$_2$ | 1 | 19.90 | 21.45 |
| 68 | (2S)-(H—Ala—His—D-2Nal-D—Phe—NH)-1,6-di-aminohexane | 8 | 17.05 | 19.07 |
| 69 | 4-(H—Ala—His—D-2Nal-D—Phe—NH)butylamine | 3 | 18.65 | 20.08 |
| 70 | 3-(H—Ala—His—D-2Nal-D—Phe—NH)-propyl-amine | 3 | 18.42 | 19.80 |
| 71 | (3-Aminomethylbenzoyl)-D-hPhe-D—Phe—Lys—NH$_2$ | 7 | 20.33 | 21.95 |
| 72 | (3-Aminomethylbenzoyl)ψ(CH$_2$NH)D-2Nal-D—Phe—Lys—NH$_2$ | 5 | 14.17 | 17.23 |
| 73 | (3-Aminomethylbenzoyl)-D-2Nal-D-hPhe-Lys—NH$_2$ | 7 | 25.30 | 26.58 |
| 74 | (3-Amino-3-methylbutanoyl)—His—D-2Nal-D—Phe—Lys—NH$_2$ | 58 | 18.12 | 20.20 |
| 75 | (3-Aminomethylbenzoyl)-D-2Nal-N—Bzl—Gly—Lys—NH$_2$ | 7 | 25.33 | 26.70 |
| 76 | (2S)-((3-Aminomethylbenzoyl)-D-2Nal-D—Phe—NH)-6-aminohexanol | 4 | 22.95 | 24.32 |
| 77 | (3-Aminomethylbenzoyl)-D-2Nal-D-Thial-Lys—NH$_2$ | 7 | 22.13 | 23.23 |
| 78 | (2S)-(H—Aib—Hisψ(CH$_2$NH)D-2Nal-D—Phe—NH)-6-aminohexanol | 59 | 12.83 | 17.27 |
| 79 | (3-Aminomethylbenzoyl)-D-2Nal-D-3Pyal-Lys—NH$_2$ | 1 | 15.10 | 16.87 |
| 80 | (3-Aminomethylbenzoyl)-D-2Nal-D—Phe(4-F)-Lys—NH$_2$ | 7 | 23.40 | 24.63 |
| 81 | (3-Aminomethylbenzoyl)-D-2Nal-D—Phe(4-OMe)-Lys—NH$_2$ | 7 | 22.50 | 23.90 |
| 82 | 2-(H—Aib—His—D-2Nal-D—Phe—NH)ethane | 3 | 18.30 | 20.47 |
| 83 | H—Aib—Phe—D-2Nal-D—Phe—Lys—NH$_2$ | 1 | 29.25 | 30.55 |
| 84 | 2-(H—Aib—His—D-2Nal-D—Phe—NH—(1-methyl-2-pyrrolidinyl)ethane | 3 | 18.70 | 20.80 |
| 85 | 2-(H—Aib—His—D-2Nal-D—Phe—NH)-(2- | 3 | 19.20 | 20.83 |

-continued

| Ex. | Peptide | Prepared using a procedure similar to example no. | RP-HPLC retention time for condition A1 (Ex. 1) | RP-HPLC retention time for condition B1 (Ex. 1) |
|---|---|---|---|---|
|  | pyridyl)ethane |  |  |  |
| 86 | (3-Aminomethylbenzoyl)—D-2Nal-N—Me—D—Phe—Lys—NH$_2$ | 1 | 26.78 | 27.88 |
| 87 | H—Aib—His—D-2Nal-D—Phe—Gly—NH$_2$ | 1 | 20.48 | 22.23 |
| 88 | H—Aib—His—D-2Nal-D—Phe—Ala—NH$_2$ | 1 | 21.65 | 23.38 |
| 89 | H—Aib—His—D-2Nal-D—Phe—Orn—NH$_2$ | 1 | 18.43 | 20.05 |
| 90 | (5-Aminomethylthienyl-2-carbonyl)-D-2Nal-D—Phe—Lys—NH$_2$ | 1 | 22.32 | 23.65 |
| 91 | H—Aib—His—D-2Nal-D—Phe—D—Lys—NH$_2$ | 1 | 18.50 | 20.00 |
| 92 | H—Aib—His—D-2Nal-D—Phe—Dab—NH$_2$ | 1 | 17.75 | 19.48 |
| 93 | H—Aib—His—D-2Nal-D—Pheψ(CH$_2$NH)Lys—NH$_2$ | 5 | 18.57 | 20.62 |
| 94 | H—Aib—His—D-2Nal-D—Phe—N—Me—Lys—NH$_2$ | 62 | 18.03 | 20.60 |
| 95 | (3-Aminomethylthienyl-2-carbonyl)-D-2Nal—D—Phe—Lys—NH$_2$ | 1 | 23.23 | 24.78 |
| 96 | H—Aib—His—D-2Nal-N—Me—D—Phe—Lys—NH$_2$ | 1 | 21.78 | 23.53 |
| 97 | H—Aib—His—D-2Nal-D—Phe—Lys—N(Me)$_2$ | 3 | 18.70 | 21.07 |
| 98 | (3-Aminomethylbenzoyl)-D-1Nal-D—Phe—Lys—NH$_2$ | 1 | 22.67 | 24.23 |
| 99 | H—Aib—His—D-2Nal-D—Trp—Lys—NH$_2$ | 1 | 18.17 | 20.40 |
| 100 | (2-Pyridylmethyl)-Aib—His—D-2Nal-D—Phe—Lys—NH$_2$ | 63 | 19.07 | 21.73 |
| 101 | H—Aib-(3-aminomethylbenzoyl)-D-2Nal-D—Phe—Lys—NH$_2$ | 7 | 23.95 | 25.38 |
| 102 | H—Aib-3Pyal-D-2Nal-D—Phe—Lys—NH$_2$ | 1 | 18.53 | 20.38 |
| 103 | (3R)-Piperidinecarbonyl)-D-2Nal-D—Phe—Lys—NH$_2$ | 1 | 21.52 | 22.97 |
| 104 | (2-(H—Aib—His—D-2Nal-NH)ethyl)benzene | 3 | 25.55 | 27.85 |
| 105 | (2R-Hydroxypropyl)-Aib—His—D-2Nal-D—Phe—Lys—NH$_2$ | 64 | 18.15 | 20.28 |
| 106 | (3-Aminomethylbenzoyl)-D-2Nal-D—Pheψ(CH$_2$NH)Lys—NH$_2$ | 5 | 22.00 | 23.95 |
| 107 | (3-Aminomethylbenzoyl)-N—Me—D-2Nal-D—Phe—Lys—NH$_2$ | 62 | 23.27 | 24.72 |
| 108 | (3-Aminomethylbenzoyl)-D-2Nal-D—Phe—N—Me—Lys—NH$_2$ | 67 | 22.60 | 23.98 |
| 109 | H—D—Thr—His—D-2Nal-D—Phe—Lys—NH$_2$ | 7 | 17.75 | 19.83 |
| 110 | H—Hyp—His—D-2Nal-D—Phe—Lys—NH$_2$ | 7 | 17.58 | 19.37 |

The structures of representative peptides of the invention are shown below.

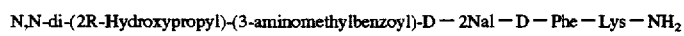

N,N-di-(2R-Hydroxypropyl)-(3-aminomethylbenzoyl)-D—2Nal—D—Phe—Lys—NH$_2$

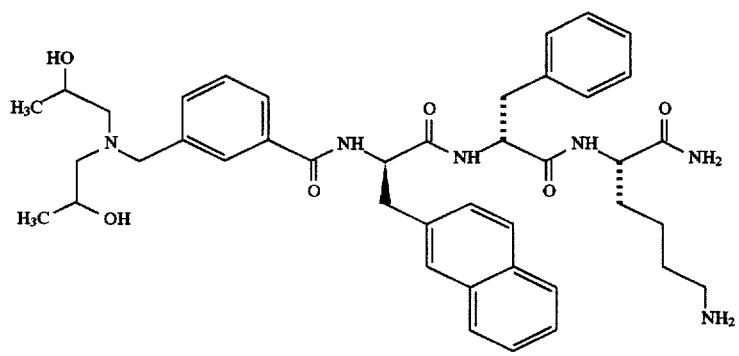

-continued
3-((4-Imidazolyl)propionyl)-D—2Nal—D—Phe—Lys—NH₂
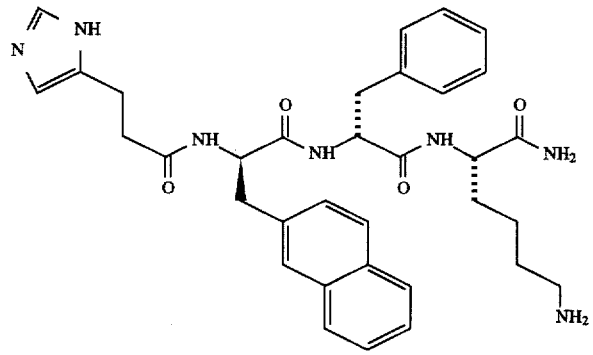
H—Ala—3Pyal—D—2Nal—D—Phe—Lys—NH₂
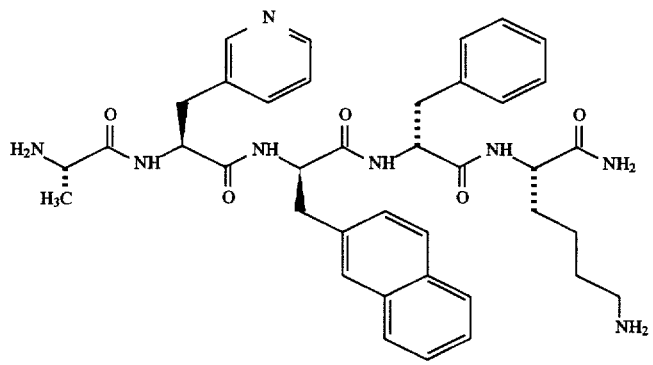
(Trans-4-aminomethylcyclohexanoyl)-D—2Nal—D—Phe—Lys—NH₂
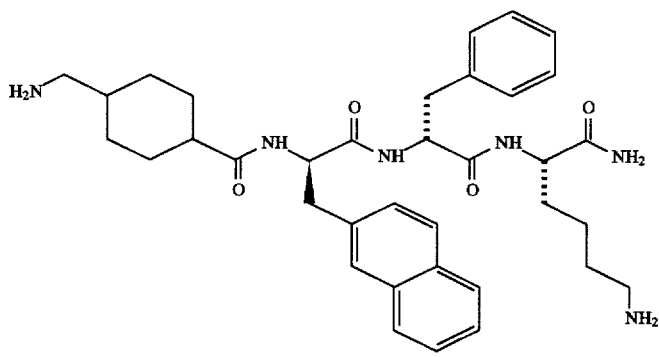
H—Ala-(2-aminobenzoyl)-D—2Nal—D—Phe—Lys—NH₂
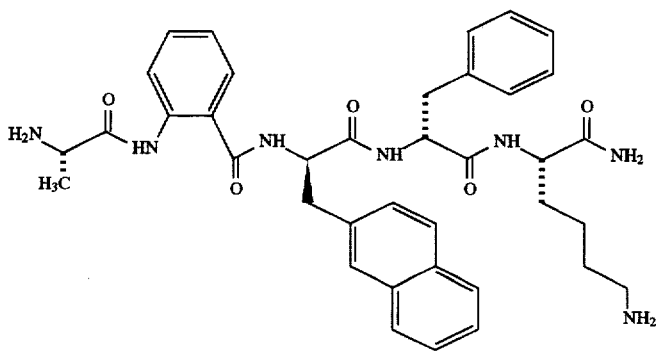

-continued
(3R)-Piperidinecarbonyl-D—2Nal—D—Phe—Lys—NH₂
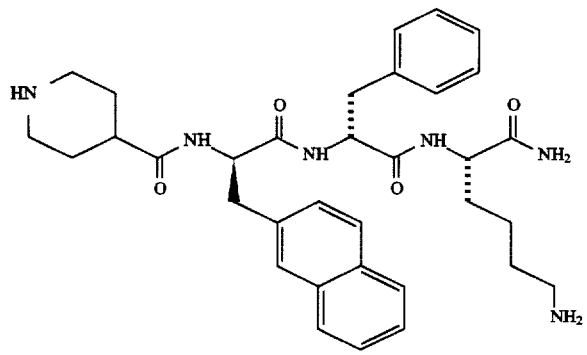
H—Ala—N—Me-(2-aminobenzoyl)-D—2Nal—D—Phe—Lys—NH₂
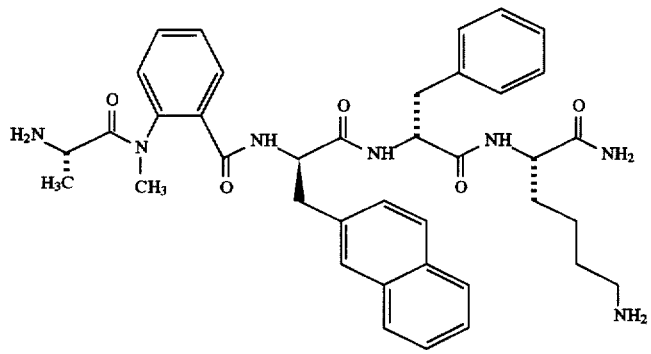
(2S)-(H—Aib—Hisψ(CH₂NH)D—2Nal—D—Phe—NH)-6-aminohexanol
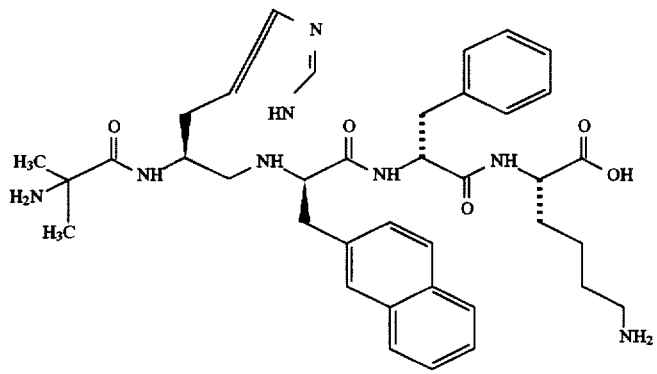
2-(H—Aib—His—D—2Nal—D—Phe—NH)(1-methyl-2-pyrrolidinyl)ethane
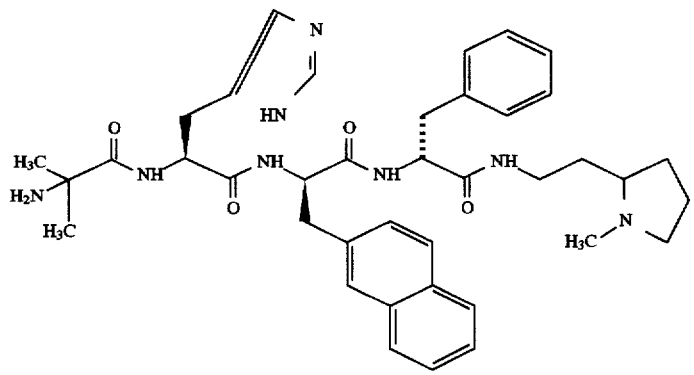

(5-Aminomethylthienyl-2-carbonyl)-D — 2Nal — D — Phe — Lys — NH$_2$

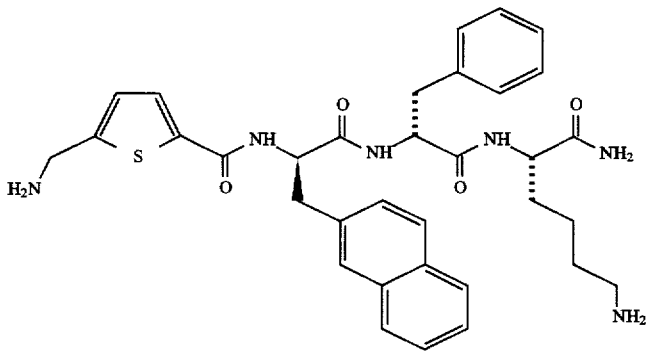

(3-Aminomethyl-thienyl-2-carbonyl)-D — 2Nal — D — Phe — Lys — NH$_2$

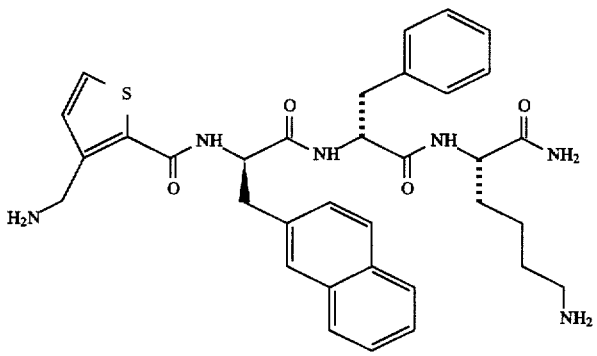

(3-Aminomethylbenzoyl)-D — 2Nal — N-(phenethyl)-Gly — Lys — NH$_2$

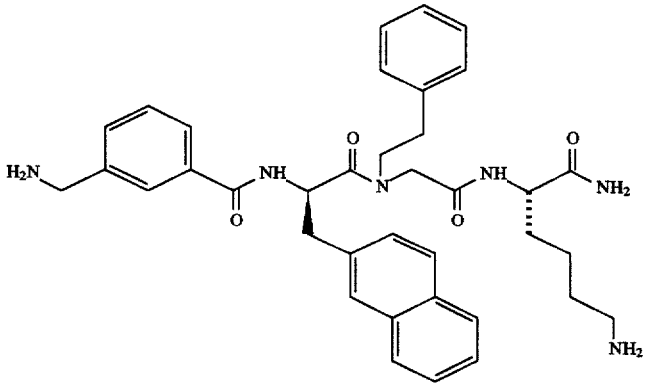

EXAMPLE 116

An in-vitro assay using rat pituitary cells was established to study the effect of different GH secretagogues. The mixed pituitary cell culture was isolated from the anterior pituitary of male rats and cultured for 3 days. After washing the cells were stimulated for 15 min and the amount of GH secreted measured in the culture supernatant.

The isolation of rat pituitary cells was a modification of 0. Sartor et al., Endocrinolog 116, 1985, pp. 952–957. Pituitaries were discharged from 250 g male Sprague-Dawley rats after decapitation. The neurointermediate lobes were removed and the remainder was placed in Grey's medium supplemented with 0.25% glucose, 2× non essential amino acid and 1% BSA (isolation buffer). The glands were cut into small pieces and transferred to a flask containing 3 ml isolation buffer+11.5 mg trypsin and 1000 μg DNase and incubated for 35 min at 37° C., 95% ° 2 and 70 rotations per min. The fragments were washed 3 times by sedimentation in isolation buffer and aspirated into single cells by using a pasteur pipet. After dispersion the cells were filtered though a nylon filter (160 jum) to remove undigested tissue. The cells were washed 3 times with isolation buffer supplemented with trypsin inhibitor (0.75 mg/ml) and resuspended in culture medium (DMEM supplemented with 25 mM HEPES, 4mM Glutamine, 0.75% sodium bicarbonate, 2.5% FCS, 3% horse serum, 10% rat serum, 1 nM T$_3$ and 40 gg/L dexamethasone) to a density of 2×105 cells/ml. The cells were seeded into microtiter plates, 200 μl/well and cultured for 3 days at 37° C.and 8% CO$_2$.

Following the culture period the cells were washed twice with stimulation buffer (HBSS supplemented with 1% BSA, 0.25% D-glucose and 25 mM HEPES) and preincubated for 1 hour. The buffer was then removed and new stimulation buffer containing the peptide was added and the plates were incubated for 15 min at 37° C.and 5% $CO_2$. The medium was collected and analyzed for rat growth hormone (rGH) content in a scintillation proximity assay (SPA) as follows (SPA, essentially as described in U.S. Pat. No. 4,568,649, Hart and Greenwalt, *Mol.Immunol.* 16, 1979, pp. 265–269, or Udenfriend et al., *Proc.Natl.Acad.Sci. USA* 82, 1985, pp. 8672–8676).

The rGH assay was performed in OptiPlates (96-well plates) suitable for direct counting in a Packards TopCount (β-scintillation counter).

Assay Protocol:

40 µl buffer
10 µl sample (incubated stimulation buffer)
50 µl $I^{125}$1-rGH
50 µl rabbit anti-rGH
50 µl SPA reagent (anti-rabbit antibody)

The plates are sealed and placed on a plate shaker for 30 minutes followed by 10 hours of incubation and settling at 10–15° C.and counting.

In the SPA, rGH bound to an anti-GH rabbit antibody (primary antibody) is reacted with a second antibody bound to fluomicrospheres (SPA Type II RIA available from Amersham). Any radiolabelled rGH which is bound to the primary antibody will be immobilized on the fluomicrospheres which will then produce light. Measurement in a β-scintillation counter makes it possible to calculate the amount of radiolabelled rGH. The amount of radiolabelled rGH bound to the fluomicrospheres decreases with an increasing content of rGH in the sample.

| Ex. No. | Compound | $EC_{50}$ (nM) | $E_{max}$ (% of GHRP-6) |
|---|---|---|---|
| 3 | H—Ala—His—D-2Nal-DPhe—NH—(CH$_2$)$_5$—NH$_2$ | 20 | 100 |
| 10 | H—Ala—Phe—D-2Nal-D—Phe—Lys—NH$_2$ | 2 | 90 |
| 51 | H—Ala—His—D-1Nal-D—Phe—Lys—NH$_2$ | 10 | 85 |
| 76 | (2S)-((3-Aminomethylbenzoyl)-D2Nal-D—Phe—NH)-6-aminohexanol | 26 | 65 |
| 83 | H—Aib—Phe—D-2Nal-D—Phe—Lys—NH$_2$ | 8 | 75 |
| 88 | H—Aib—His—D-2Nal-D—Phe—Ala—NH$_2$ | 11 | 80 |
| 104 | (2-(H—Aib—His—D-2Nal-NH)ethyl)benzene | 58 | 85 |

We claim:

1. A compound of general formula I $$A\text{-}B\text{-}C\text{—}D(\text{—}E)_p \qquad I$$

wherein p is 0 or 1;

A is hydrogen or $R^1$—$(CH_2)_q$—$(X)_r$—$(CH_2)_s$—CO—, wherein
q is 0 or an integer from 1 to 5;
r is 0 or 1;
s is 0 or an integer from 1 to 5;
$R^1$ is hydrogen, imidazolyl, guanidino, piperazino, morpholino, piperidino or $N(R^2)$—, wherein each of $R^2$ and $R^3$ is independently hydrogen or lower alkyl optionally substituted by one or more hydroxyl, pyridinyl or furanyl groups; and X, when r is 1, is —NH—, —$CH_2$—, —CH=CH—,

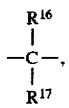

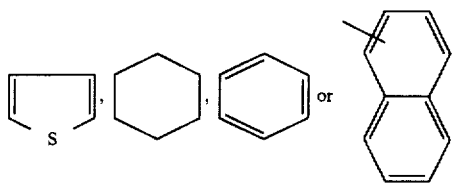

wherein each of which is disubstituted; B is $(G)_t$—$(H)_u$ wherein
t is 0 or 1;
u is 0 or 1;
G and H are amino acid residues selected from the group consisting of natural L-amino acids or their corresponding D-isomers, and non-natural amino acids and wherein, when both t and u are 1, the amide bond between G and H is optionally replaced with

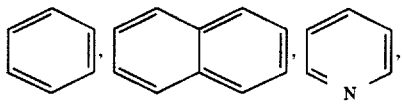

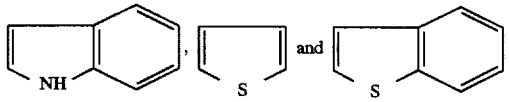

each of which is optionally substituted with halogen, lower alkyl, lower alkyloxy, lower alkylamino, amino or hydroxy;

D, when p is 1, is a D-amino acid of formula —NH—CH(($CH_2$)$_k$—$R^5$)—CO— or, when p is 0,
D is —NH—CH(($CH_2$)$_l$—$R^5$)—$CH_2$—$R^6$ or —NH—CH(($CH_2$)$_m$—$R^5$)—CO—$R^6$, wherein
k is 0, 1 or 2;
l is 0, 1 or 2;
m is 0, 1 or 2;
$R^5$ is selected from the group consisting of

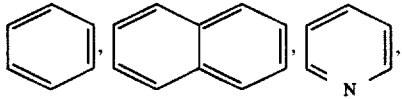

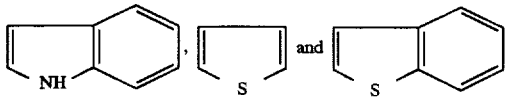

each of which is optionally substituted with halogen, alkyl, alkyloxy, amino or hydroxy; and
$R^6$ is piperazino, morpholino, piperidino, —OH or —N($R^7$)—$R^8$, wherein each of $R^7$ and $R^8$ is independently hydrogen or lower alkyl;

E. when p is 1, is —NH—CH(R¹⁰)—(CH₂)ᵥ —R⁹, wherein v is 0 or an integer from 1 to 8;

R⁹ is hydrogen, idazolyl, guanidino, piperazino, morpholino, 1-methylpyrrolidinyl, piperidino,

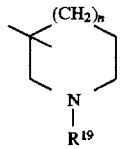

wherein n is 0, 1 or 2, and R¹⁹ is hydrogen or lower alkyl,

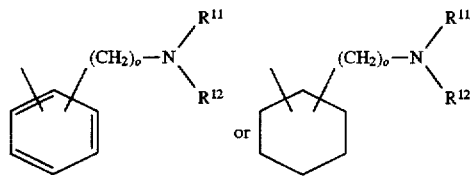

wherein o is an integer from 1 to 3, wherein the morpholino is optionally substituted with ethyl or propyl and the 1-methylpyrrolodinyl group is optionally substituted with ethyl, or R⁹ is N(R¹¹)—R¹², each of R¹¹ and R¹² is independently hydrogen or lower alkyl, or R⁹ is independently

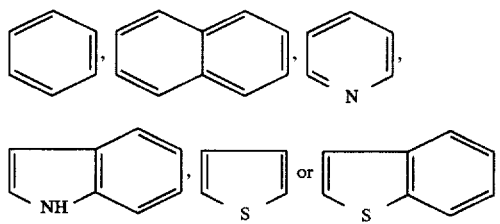

each of which is optionally substituted with halogen, alkyl, alkyloxy, amino, alkylamino, hydroxy, or the Amadori rearrangement product from an amino group and a hexapyranose or a hexapyranosyl-hexapyranose and R¹⁰, when p is 1, is selected from the group consisting of —H, —COOH, —CH₂—, CO—R¹³ and —CH₂—OH, wherein R¹³ is piperazino, morpholino, piperidino, —OH or —N(R¹⁴)—R¹⁵, wherein each of R¹⁴ or R¹⁵ is independently hydrogen and lower alkyl;

with the proviso that, when R⁹ is phenyl, indolyl, or hydroxyphenyl, then R¹⁰ is different from —COOH, CH₂—OH and —CO—R¹³, wherein R¹³ is —N(R¹⁴)—R¹⁵, the amide bond between B and C or, when t and u are both 0, between A and C being optionally replaced with

or, when p is 1, the amide bond between D and E being optionally replaced with

2. The compound according to claim 1, in which G and H are non-natural amino acids selected from the group consisting of 1,4-diaminobutyric acid, amino-isobutyric acid, 1,3-diaminopropionic acid, 4-aminophenylalanine, 3-pyridylalanine, 1,2,3,4-tetrahydroisoquinoline-3-carboxylic acid, 1,2,3,4-tetrahydronorharman-3-carboxylic acid, N-methylanthranilic acid, anthranilic acid, N-benzylglycine, 3-amino-3-methylbenzoic acid, 3-amino-3-methyl butanoic acid, sarcosine, nipecotic acid and iso-nipecotic acid.

3. The compound according to claim 1, wherein p is 1.

4. The compound according to claim 1, wherein A is hydrogen.

5. The compound according to claim 1, wherein A is $R^1$—$(CH_2)_q$—$(X)_r$—$(CH_2)_s$—$CO$—, wherein $R^1$ is 3-imidazolyl, q is 2, r is 0 and s is 0; or wherein $R^1$ is $NH_2$, q is 1, r is 1, X is disubstituted benzene substituted in the 1 and 3 positions, and s is 0; or wherein $R^1$ is $NH_2$, q is 1, r is 1, X is disubstituted thiophene substituted in the 3 and 2 positions, and s is 0.

6. The compound according to claim 1, wherein, when t is 1, G is Ala, Gly, Aib, sarcosine, nipecotic acid, or iso-nipecotic acid.

7. The compound according to claim 1, wherein, when u is 1, H is His, Phe, Tic, 3Pyal, Gly, Ala, Phe(4-NH₂), Sar, Pro, Tyr, Arg, Orn, 3-aminomethylbenzoic acid or D-Phe.

8. The compound according to claim 1, wherein R⁴ is 2-naphthyl.

9. The compound according to claim 1, wherein R⁵ is phenyl.

10. The compound according to claim 1, wherein v is 2–6, and R⁹ is —NH₂, morpholinopropane, morpholinoethyl or (1-methylpyrrolidinyl)ethane.

11. The compound according to claim 1, wherein R¹⁰ is —COOH, CH₂—OH, —H or CONH₂.

12. A compound for treating medical disorders resulting from a deficiency in growth hormone selected from the group consisting of H-Ala-His ψ(CH₂NH)D-2Nal-D-Phe-Lys-NH₂
H-Ala-Ala-D-2Nal-D-Phe-Lys-NH₂
H-His-D-2Nal-D-Phe-Lys-NH₂
(3 -(4-Imidazolyl)propionyl)-D-2Nal-D-Phe-Lys-NH₂
H-D-Lys-D-2Nal-D-Phe-Lys-NH₂
H-5Apent-His-D-2Nal-D-Phe-Lys-NH₂
H-D-Ala-D-2Nal-D-Phe-Lys-NH₂
H-5Apent-D-2Nal-D-Phe-Lys-NH₂
(n-Propyl)-His-D-2Nal-D-Phe-Lys-NH₂
H-Ala-3Pyal-D-2Nal-D-Phe-Lys-NH₂
-Ala-Phe(4-NH₂)-D-2Nal-D-Phe-Lys-NH₂
H-D-Ala-His-D-2Nal-D-Phe-Lys-NH₂
(2-(4-Imidazolyl)acetyl)-D-2Nal-D-Phe-Lys-NH₂
(3 -(4-Imidazolyl)acryloyl)-D-2Nal-D-Phe-Lys-NH₂
(3-Aminomethyl benzoyl)-D-2Nal-D-Phe-Lys-NH₂
(3-Aminophenylacetyl)-D-2Nal-D-Phe-Lys-NH₂
(4-Aminophenylacetyl)-D-2Nal-D-Phe-Lys-NH₂
(3 -Aminocrotonoyl)-D-2Nal-D-Phe-Lys-NH₂
(4-Piperidino-carboxyl)-D-2Nal-D-Phe-Lys-NH₂
H-Ala-H is-D-2Nal-D-Phe-NH₂
(H-Ala-His-D-2Nal-D-Phe-NH)hexane 6-(H-Ala-His-D-2Nal-D-Phe-NH)hexylamine
5-(H-Ala-His-D-2Nal-D-Phe-NH)pentylanaine
H-Ala-His-D-2Nal-D-Pheψ(CH$_2$NH)Lys-NH$_2$
H-Ala-His-D-2Nal-D-Phe-Lys-OH
(2S)-(H-Ala-His-D-2Nal-D-Phe-NH)-6-aminohexanol
(2-(H-Ala-His-D-2Nal-D-Phe-NH)ethyl)benzene
2-(H-Ala-His-D-2Nal-D-Phe-NH)ethylamine
4-((H-Ala-His-D-2Nal-D-Phe-NH)methyl)benzylamine
H-Ala-His-D-2Nal-D-Phe-Lys(maltosyl)-NH$_2$
H-Ala-His-D-Phe-D-Phe-Lys-NH$_2$
H-Ala-His-D-Trp-D-Phe-Lys-NH$_2$
H-His-D-2Nal-D-Trp-Lys-NH$_2$
H-Ala-His-D-1Nal-D-Phe-Lys-NH$_2$
H-Ala-Phe-D-2Nal-D-Phe-Lys-NH$_2$
H-Ala-His-D-2Nal-D-Phe-Lys(maltosyl)-NH$_2$
(2R)-(H-Ala-His-D-2Nal-D-Phe-Lys-NH)-3phenylpropylamine
H-Ala-N-Me-(2-aminobenzoyl)-D-2Nal-D-Phe-Lys-NH$_2$
(3-(Methylaminomethyl)benzoyl)-D-2Nal-D-Phe-Lys-NH$_2$
(4-(Aminomethyl)benzoyl)-D-2Nal-D-Phe-Lys-NH$_2$
H-His-Ala-D-2Nal-D-Phe-Lys-NH$_2$
4-(H-Ala-His-D-2Nal-D-Phe-NH)butylamine
3-(H-Ala-His-D-2Nal-D-Phe-NH)propylamine
(3-(Dimethylaminomethyl)benzoyl)-D-2Nal-D-Phe-Lys-NH$_2$
(3-Amino-3-methylbutanoyl)-D-2Nal-D-Phe-Lys-NH$_2$
(3-Aminomethylbenzoyl)-D-hPhe-D-Phe-Lys-NH$_2$
(3-Aminomethylbenzoyl)ψ(CH$_2$NH)D-2Nal-D-Phe-Lys-NH$_2$
(3-Aminomethylbenzoyl)-D-2Nal-D-hPhe-Lys-NH$_2$
(3-Amino-3-methylbutanoyl)-His-D-2Nal-D-Phe-Lys-NH$_2$
(3-Aminomethylbenzoyl)-D-2Nal-N-Bzl-Gly-Lys-NH$_2$
(2S)-((3-aminomethylbenzoyl)ψ(CH$_2$NH)-D-2Nal-D-Phe-NH)-6-aminohexanol
($^2$S)-(($^3$-aminomethylbenzoyl)-D-2Nal-D-Phe-NH)-6-aminohexanol
(3-Aminomethylbenzoyl)-D-2Nal-D-Thial-Lys-NH$_2$
($^2$S)-(H-Aib-Hisψ(CH$_2$NH)-D-2Nal-D-Phe-NH)-6-aminohexanol
(3-Aminomethylbenzoyl)-D-2Nal-D-3Pyal-Lys-NH$_2$
(3-Aminomethylbenzoyl)-D-2Nal-D-Phe(4-F)-Lys-NH$_2$
(3-Aminomethylbenzoyl)-D-2Nal-D-Phe(4-OMe)-Lys-NH$_2$
(2-Aminomethylphenylacetyl)-D-2Nal-D-Phe-Lys-NH$_2$
(2-Aminomethylbenzoyl)-D-2Nal-D-Phe-Lys-NH$_2$
2-(H-Aib-His-D-2Nal-D-Phe-NH)-(4-pyridyl)ethane
H-Aib-Phe-D-2Nal-D-Phe-Lys-NH$_2$
2-(H-Aib-His-D-2Nal-D-Phe-NH)-(1-methyl-2-pyrrolidinyl)ethane
2-(H-Aib-His-D-2Nal-D-Phe-NH)-(4-pyridyl)ethane
H-Aib-Hisψ(CH$_2$NH)-D-2Nal-D-Phe-Lys-OH
(3-Aminomethylbenzoyl)-D-2Nal-N-Me-D-Phe-Lys-NH$_2$
H-Aib-His-D-2Nal-D-Phe-Gly-NH$_2$
H-Aib-His-D-2Nal-D-Phe-Ala-NH$_2$
H-Aib-His-D-2Nal-D-Phe-Orn-NH$_2$
(5-Aminomethylthienyl-2-carbonyl)-D-2Nal-D-Phe-Lys-NH$_2$
H-Aib-His-D-2Nal-D-Phe-D-Lys-NH$_2$
H-Aib-His-D-2Nal-D-Phe-Dab-NH$_2$
H-Aib-His-D-2Nal-D-Pheψ(CH$_2$NH)-Lys-NH$_2$
H-Aib-His-N-Me-D-2Nal-D-Phe-Lys-NH$_2$
H-Aib-His-D-2Nal-D-Phe-Lys-NH$_2$
H-Aib-His-D-2Nal-D-Phe-N-Me-Lys-NH$_2$
(3-Aminomethylthienyl-2-carbonyl)-D-2Nal-D-Phe-Lys-NH$_2$
H-Aib-His-D-2Nal-N-Me-D-Phe-Lys-NH$_2$
H-Aib-His-D-2Nal-D-Phe-Lys-N(Me)$_2$
(3R)-Piperidinecarbonyl-D-2Nal-D-Phe-Lys-NH$_2$
(3S)-Piperidinecarbonyl-D-2Nal-D-Phe-Lys-NH$_2$
(3-Aminomethylbenzoyl)-D-1Nal-D-Phe-Lys-NH$_2$
H-Aib-His-D-2Nal-D-Trp-Lys-NH$_2$
(Furfuryl)-Aib-His-D-2Nal-D-Phe-Lys-NH$_2$
(2-Pyridylmethyl)-Aib-His-D-2Nal-D-Phe-Lys-NH$_2$
H-Aib-(3-aminomethylbenzoyl)-D-2Nal-D-Phe-Lys-NH$_2$
H-Aib-3Pyal-D-2Nal-D-Phe-Lys-NH$_2$
(3S)-Piperidinecarbonyl-D-2Nal-D-Phe-Lys-NH$_2$
(3R)-Piperidinecarbonyl-D-2Nal-D-Phe-Lys-NH -
(2-(H-Aib-His-D-2Nal-NH)ethyl)benzene
N,N-di(2R-Hydroxypropyl)-(3-aminomethylbenzoyl)-D-2Nal-D-Phe-Lys-NH$_2$
(2R-Hydroxypropyl)-Aib-His-D-2Nal-D-Phe-Lys-NH$_2$
(3-Aminomethylbenzoyl)-D-2Nal-D-Pheψ(CH$_2$NH)Lys-NH$_2$
(3-Aminomethylbenzoyl)-N-Me-D-2Nal-D-Phe-Lys-NH$_2$
(3-Aminomethylbenzoyl)-D-2Nal-D-Pbe-N-Me-Lys-NH$_2$
H-D-Thr-His-D-2Nal-D-Phe-Lys-NH$_2$
H-Aib-His-D-2Nal-N-(phenethyl)-Gly-Lys-NH$_2$
(3-Aminomethylbenzoyl)-D-2Nal-N-(phenethyl)-Gly-Lys-NH$_2$
H-Hyp-His-D-2Nal-D-Phe-Lys-NH$_2$
H-Aib-His-N-Me-D-2Nal-N-(phenethyl)-Gly-Lys-NH$_2$
H-Aib-His-N-Me-D-2Nal-N-Me-D-Phe-Lys-NH$_2$
H-Aib-His-D-2Nal-D-Pheψ(CH$_2$N(Me))Lys-NH$_2$
3-(H-Aib-His-D-2Nal-N-Me-D-Phe-NH)morpholinopropane
2-(H-Aib-His-D-2Nal-N-Me-D-Phe-NH)-(1-methyl-2-pyrrolidinyl)ethane
(3R)-Piperidinecarbonyl-N-Me-D-2Nal-N-Me-D-Phe-Lys-NH$_2$
3-((Aminomethylbenzoyl)-D-2Nal-N-Me-D-Phe-NH)morpholinopropane
2-(H-Aib-His-N-Me-D-2Nal-N-Me-D-Phe-NH)-(1-methyl-2-pyrrolidinyl)ethane
2-(3R)-Piperidinecarbonyl-N-Me-D-2Nal-N-Me-D-Phe-NH)-(1-methyl-2-pyrrolidinyl)ethane
2-((3-Aminomethylbenzoyl)-N-Me-D-2Nal-N-Me-D-Phe-NH)-(1-methyl-2-pyrrolidinyl)ethane
3-(H-Aib-His-N-Me-D-2Nal-N-Me-D-Phe-NH)morpholinopropane
3-((3R)-Piperidinecarbonyl-N-Me-D-2Nal-N-Me-D-Phe-NH)morpholinopropane 3-((3-Aminomethylbenzoyl)-N-Me-D-2Nal-N-Me-D-Phe-NH)morpholinopropane H-A Aib-His-D-2Nal -N-Me-D-Phe-Hyp-NH$_2$ 2-((3-Aminomethylbenzoyl)-D-2Nal-N-Me-D-Phe-NH)-(1-methyl-2-pyrrolidinyl)ethane and 2-((3R)Piperidinecarbonyl-D-2Nal-N-Me-D-Phe-NH)-(1-methyl-2-pyrrolidinyl)ethane.

13. A pharmaceutical composition comprising, as an active ingredient, the compound of claim 1 or a pharmaceutically acceptable salt thereof together with a pharmaceutically acceptable carrier or diluent.

14. A composition according to claim 13 in unit dosage form, comprising from about 10 to about 200 mg of the compound of the general formula I or a pharmaceutically acceptable salt thereof.

15. A pharmaceutical composition for stimulating the release of growth hormone from the pituitary, the composition comprising, as an active ingredient, the compound of claim 1 or a pharmaceutically acceptable salt thereof together with a pharmaceutically acceptable carrier or diluent.

16. A method of stimulating the release of growth hormone from the pituitary, the method comprising administering to a subject in need thereof an effective amount of the compound of claim 1 or a pharmaceutically acceptable salt thereof.

17. The method according to claim 16, wherein the effective amount of the compound of the general formula I or pharmaceutically acceptable salt or ester thereof is in the range of from about 0.0001 to about 100 mg/kg body weight per day.

18. The method according to claim 16, wherein the effective amount of the compound of the general formula I or pharmaceutically acceptable salt or ester thereof is in the range of from about 0.001 to about 50 mg/kg body weight per day.

* * * * *

UNITED STATES PATENT AND TRADEMARK OFFICE
CERTIFICATE OF CORRECTION

PATENT NO. : 5,767,085
DATED : June 16, 1998
INVENTOR(S) : Johansen et al.

It is certified that error appears in the above-identified patent and that said Letters Patent is hereby corrected as shown below:

Column 3,
Line 20, delete "l" and insert -- l is 0, 1 or 2; --
Line 47, delete "1$^{19}$"

Column 4,
Line 1, delete "$R^{11}$ and $R^{12}$" and insert -- each of "$R^9$ --
Line 35 delete "Y is >C=or" and insert -- Y is >C=O or --

Column 5,
Line 5, delete "an d" and insert -- and --
Line 6, delete "t he" and insert -- the --
Line 12-13, delete "$R^1$-(CH$_2$), a-(X)$_r$-(CH$_2$),-CO- " insert
-- $R^1$-(CH$_2$)$_q$-(X)$_r$-(CH$_2$),-CO- --
Line 14, delete "NH$_2$" and insert -- $_2$ --
Line 22, delete "4-NH" and insert -- $_2$ --
Line 33, delete "ehtyl" and insert -- ethyl --
Line 49, delete "$R^1$" and insert -- $R^5$ --
Line 51, delete "$R^1$" and insert -- $R^{10}$ --

Column 6,
Line 3, delete "NH$_t$" and insert -- NH$_2$ --
Line 14, delete "(CH, NH)" and insert -- (CH$_2$NH) --
Line 66, delete "*" and insert -- y --

Column 7,
Line 4, delete "*" and insert -- y --
Line 6, delete "$^3$-Amino" and insert -- (3-Amino) --
Line 20, delete "MSy(CH, NH) and insert -- (CH$_2$NH) --
Line 21, delete "(3-Am inomethybenzoyl)" and insert -- (3-Aminomethybenzoyl) --

Column 8,
Line 37, delete "Thial=cthienylalanine" and insert -- Thial=thienylalanine --
Line 38, delete "hp he homo-phenylalanine" and insert -- hPhe = homo-phenylalanine --
Line 40, delete "benyiglycine" and insert -- N-benzylglcine --
Line 44, delete "10 Orn=ornithine" and insert -- Orn = ornithine --

Column 9,
Line 1, delete "b e prepare d" and insert -- be prepared --
Line 14, start new paragraph at -- Pharmaceutical...--

Page 1 of 4

UNITED STATES PATENT AND TRADEMARK OFFICE
CERTIFICATE OF CORRECTION

PATENT NO. : 5,767,085
DATED : June 16, 1998
INVENTOR(S) : Johansen et al.

It is certified that error appears in the above-identified patent and that said Letters Patent is hereby corrected as shown below:

Column 11,
Line 13, delete "a alkali" and insert -- as an alkali --

Column 12,
Line 2, delete "t al." and insert -- et al. --
Line 5, delete "H" and insert -- the --
Line 28, delete "anaesthesized" and insert -- anesthesized --
Line 32, after "administered" insert -- by --

Column 15,
Line 44, delete 4-(1,2',4'-dimethoxyphenyl) and insert -- 4-((2',4'-dimethoxyphenyl) --

Column 16,
Line 31, delete "HMO" and insert -- $H_2O$ --
Line 34, delete "C18 silica 5 cartridge" and insert -- C18 silica cartridge --
Line 35, delete "T2A" and insert -- TFA --
Line 49, delete "$SO_{4\ 1}$ Which" and insert -- $SO_4$, which --
Lines 54-55, delete "$CH_3CN$ i 0.1% T iA i H w t an d" and insert -- $CH_3CN$ / 0.1% TFA / $H_2O$ and --
Line 58-59, delete "Bi was found to be 17.88 m i" and insert -- B1 was found to be 17.88 min --

Column 17,
Line 7, delete "Bi" and insert -- B1 --
Lines 39-40, delete "A land B 1" and insert -- A1 and B1 --

Column 18,
Line 42, delete "Bi" and insert -- B1 --

Column 20,
Line 35, insert -- Examples 9-54 --

Column 24,
Line 19, delete "150 =82 1 $H_2O$ and insert -- 150 µl $H_2O$ --

Column 25,
Line 9, delete "4-((2, 4'-4"-dimethoxyphenyl)" and insert -- 4-((2',4'-dimethyoxyphenyl) --

UNITED STATES PATENT AND TRADEMARK OFFICE
CERTIFICATE OF CORRECTION

PATENT NO. : 5,767,085
DATED : June 16, 1998
INVENTOR(S) : Johansen et al.

It is certified that error appears in the above-identified patent and that said Letters Patent is hereby corrected as shown below:

Column 26,
Line 18, delete "The N-di-alkylated" and insert -- The N,N-di-alkylated --
Line 21, delete "RP-PLC" and insert -- RP-HPLC --

Column 33,
Line 60, delete "23.40 m i" and insert -- 2340 min --

Column 34,
Line 52, delete "95% °$_2$" and insert -- 95% $O_2$ --
Line 56, delete "(160 jum)" and insert -- (160 $\mu$m) --
Line 61, delete "40 gg/L" and insert -- 40 $\mu$g/L --
Line 62, delete "2x10" and insert -- $2 \times 10^5$ --

Column 35,
Line 19, delete "50 $\mu$l I$^{25}$ 1-rGH" and insert -- 50 $\mu$l $^{125}$I-rGH --

Claims,
Claim 1, column 35,
Line 64, delete "N($R^2$)-," and insert -- N($R^2$)-$R^3$, --

Claim 1, column 36,
Line 6, after "$R^{17}$," insert -- wherein each of $R^{16}$ and $R^{17}$ is independently hydrogen or lower alkyl; or X is --
Line 30, after "-Y-N," insert -- wherein Y is C=O or $CH_2$, and $R^{18}$ is hydrogen, lower alkyl or lower aralkyl; C is a D-amino acid of formula -NH-CH(($CH_2$)$_w$-$R^4$)-CO- wherein w is 0, 1 or 2; and $R^4$ is selected from the group consisting of --

Claim 1, column 37,
Line 4, delete "idazolyl" and insert -- imidazolyl --
Line 49, delete "-$CH_2$-, CO-R13" and insert -- -$CH_2$-$R_{13}$, -CO-$R^{13}$ --
Line 54, delete "hydrogen or" and insert -- hydrogen and --
Line 63, after "-Y-N," insert -- wherein Y is C=O or $CH_2$, and $R^{18}$ is hydrogen, lower alkyl or lower aralkyl, --

Claim 1, column 38,
Line 4, after "-Y-N," insert -- wherein Y and $R^{18}$ are as indicated above; or a pharmaceutically acceptable salt thereof --

Claim 12, column 38,
Line 56, before "-Ala" and insert -- H --

UNITED STATES PATENT AND TRADEMARK OFFICE
CERTIFICATE OF CORRECTION

PATENT NO. : 5,767,085
DATED : June 16, 1998
INVENTOR(S) : Johansen et al.

It is certified that error appears in the above-identified patent and that said Letters Patent is hereby corrected as shown below:

Claim 12, column 39,
Lines 1 and 6, change "A la-H is" to -- Ala-His --
Line 8, change "H is" to -- His --
Line 43, delete "(2$^S$)-(($^3$-" and insert -- (2S)-((3- --
Line 46, delete "($^2$S)" and insert -- (2S) --

Claim 12, column 40,
Line 27, delete "Lys-NH" and insert "Lys-NH$_2$"
Line 32, delete "Phe y" and insert -- Phey•--
Line 37, change "Pbe" to insert -- Phe --
Line 61, change "I-methyl" to -- 1-methyl --

Claim 12, column 41,
Line 3, change "H -A Aib" to -- H-Aib --

Signed and Sealed this

Thirtieth Day of October, 2001

Attest:

NICHOLAS P. GODICI
Acting Director of the United States Patent and Trademark Office

*Attesting Officer*